United States Patent [19]

McGady et al.

[11] 4,067,691
[45] Jan. 10, 1978

[54] STERILIZING SYSTEM AND AUTOMATIC CONTROL THEREFOR

[75] Inventors: Donald L. McGady, Darien; Thomas M. Hooper, Lemont; Joseph E. Wilczynski, Chicago, all of Ill.

[73] Assignee: Mercy Hospital and Medical Center, Chicago, Ill.

[21] Appl. No.: 677,842

[22] Filed: Apr. 16, 1976

[51] Int. Cl.² .............................................. A61L 3/00
[52] U.S. Cl. ........................................ 21/56; 21/81; 21/96; 21/103; 21/2
[58] Field of Search ...................... 21/56, 2, 80, 81, 96, 21/103

[56] References Cited

U.S. PATENT DOCUMENTS

| 2,509,258 | 5/1950 | Wing | 21/80 |
| 3,450,489 | 6/1969 | Fay | 21/56 X |
| 3,982,893 | 9/1976 | Joslyn | 21/2 |

FOREIGN PATENT DOCUMENTS

| 1,930,731 | 12/1970 | Germany | 21/56 |
| 1,086,661 | 10/1967 | United Kingdom | 21/56 |

*Primary Examiner*—R.E. Serwin
*Attorney, Agent, or Firm*—Hill, Gross, Simpson, Van Santen, Steadman, Chiara & Simpson

[57] ABSTRACT

A sterilizing system for sterilizing large quantities of articles used in a hospital environment incorporates sterilizing apparatus interconnected between a contaminated area and a clean area, with a double partition separating a neutral zone, in which the sterilizing apparatus is located, from the contaminated area and from the clean area. The sterilizing apparatus incorporates a vessel adapted to be heated and pressurized, and electrically operated controls spaced above the vessel for controlling the operation of the apparatus during a sterilizing process, such controls being accessible for maintenance and repair activities within the neutral zone. An automatic controller for the sterilizing system includes sensing devices for monitoring the progress of the sterilization process on a step by step basis, and furnishing signals to the various electrically operated controls to initiate each step of the sterilizing process when the preceding step is completed. In response to the occurrence of a malfunction in the sterilizing system, the controller prevents further operation of the system and signals an alarm condition. A printer associated with the computer prints out a record of the time at which each step is performed so that proper operation of the apparatus can be verified.

Apparatus is provided for insuring that a quality assurance cycle is conducted periodically and such cycle must be successfully completed before the equipment can be returned to automatic service. Following any maintenance procedures, an equipment test cycle must be successfully performed, followed by a quality assurance cycle, before automatic operation can resume.

24 Claims, 18 Drawing Figures

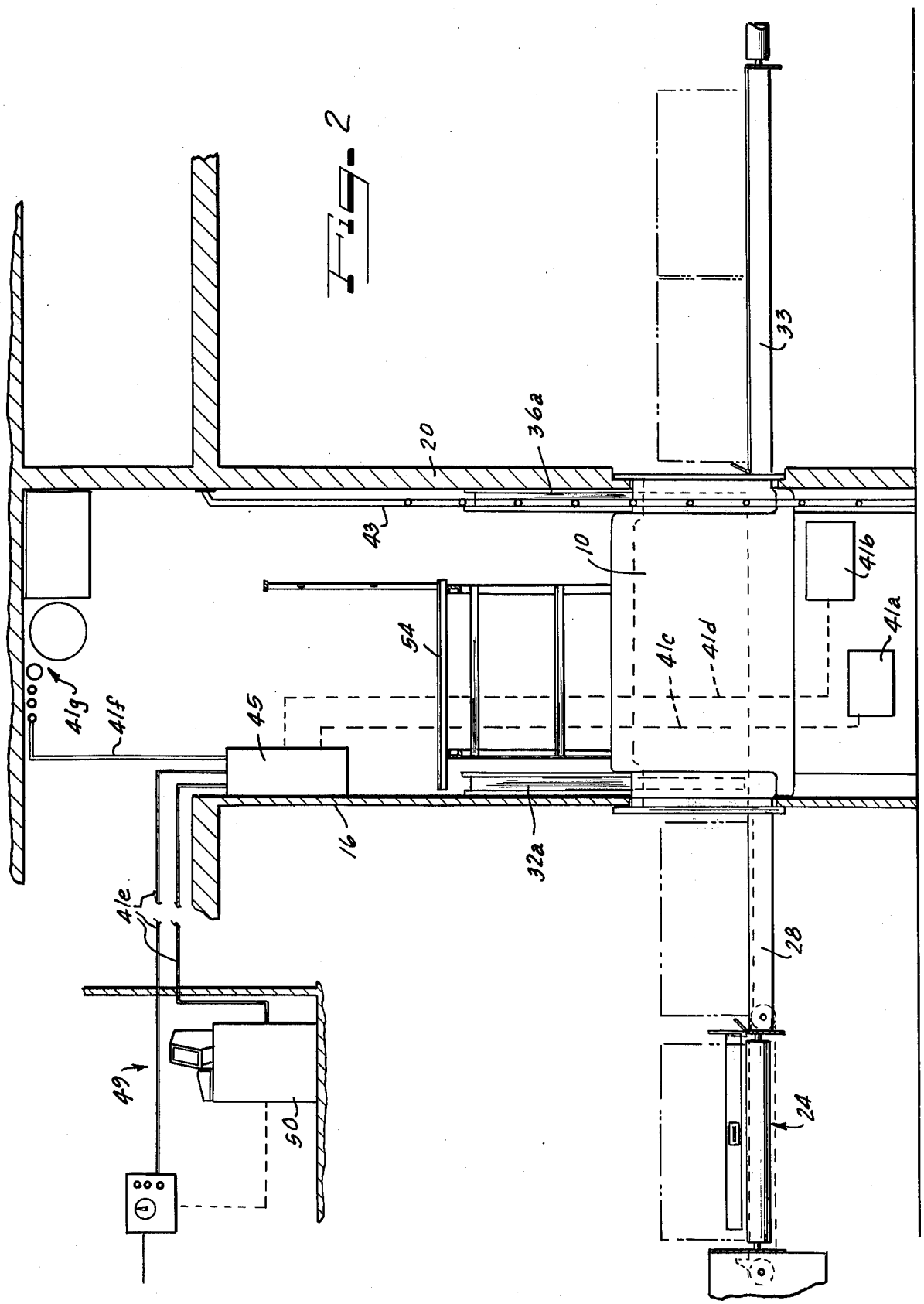

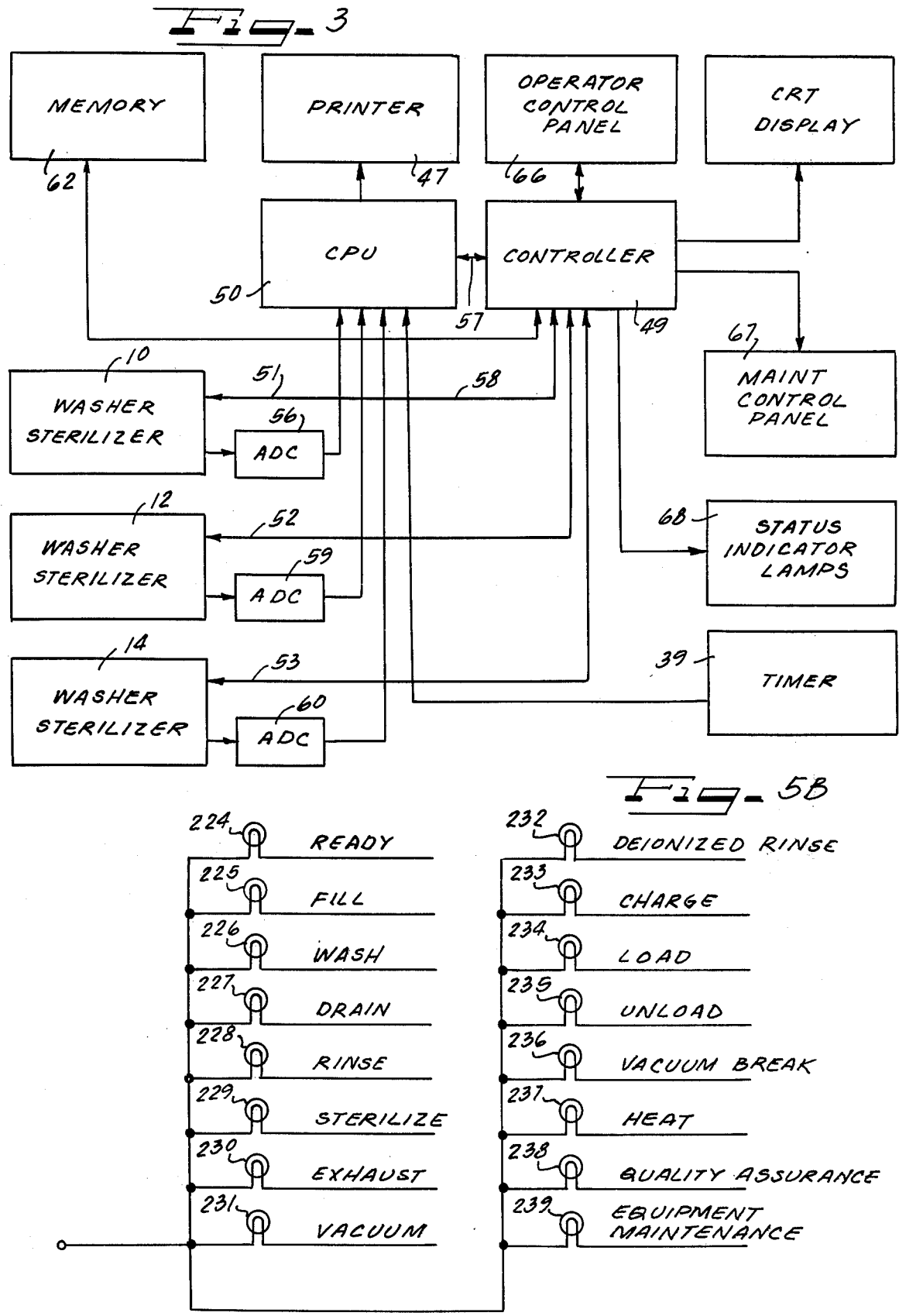

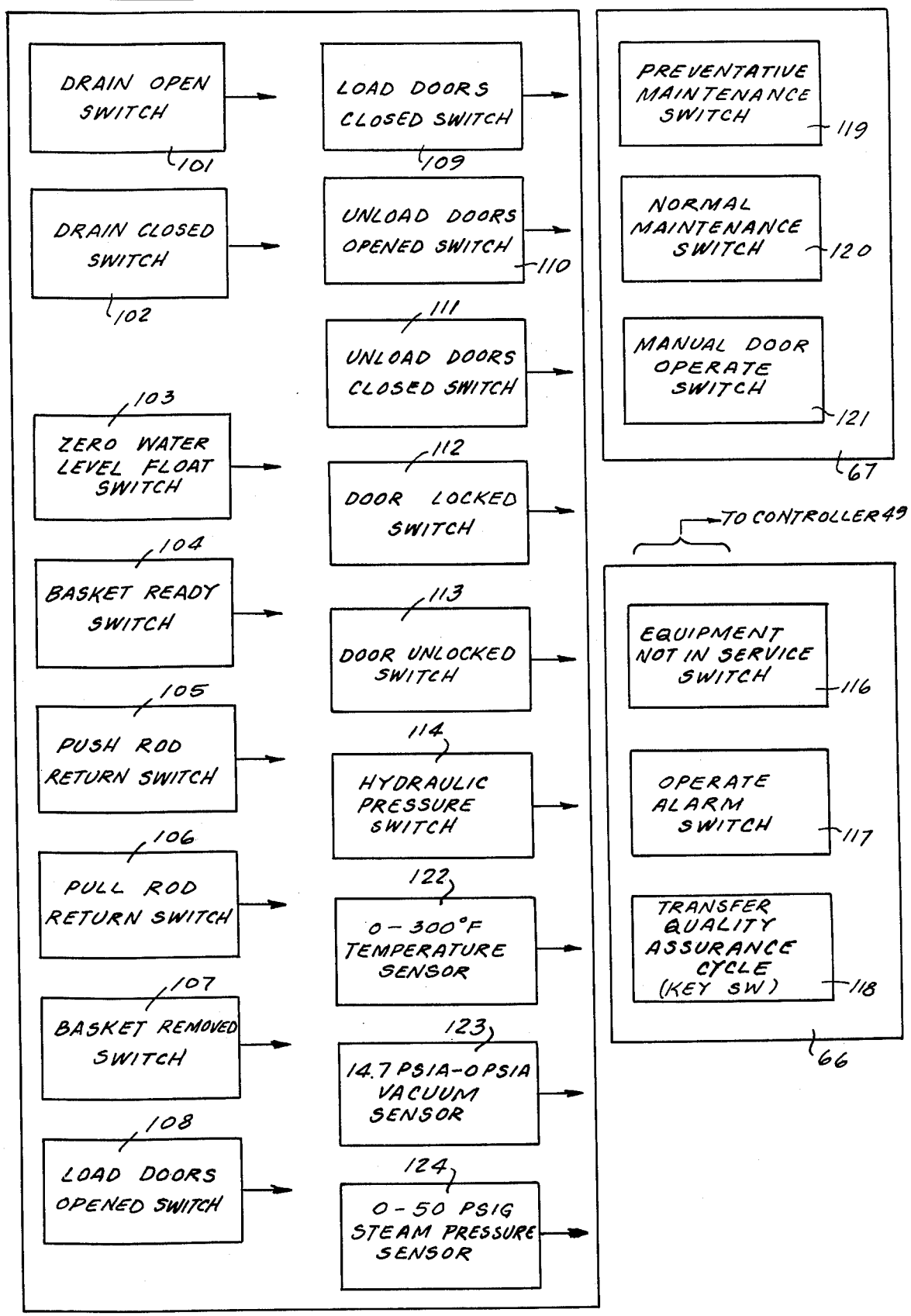

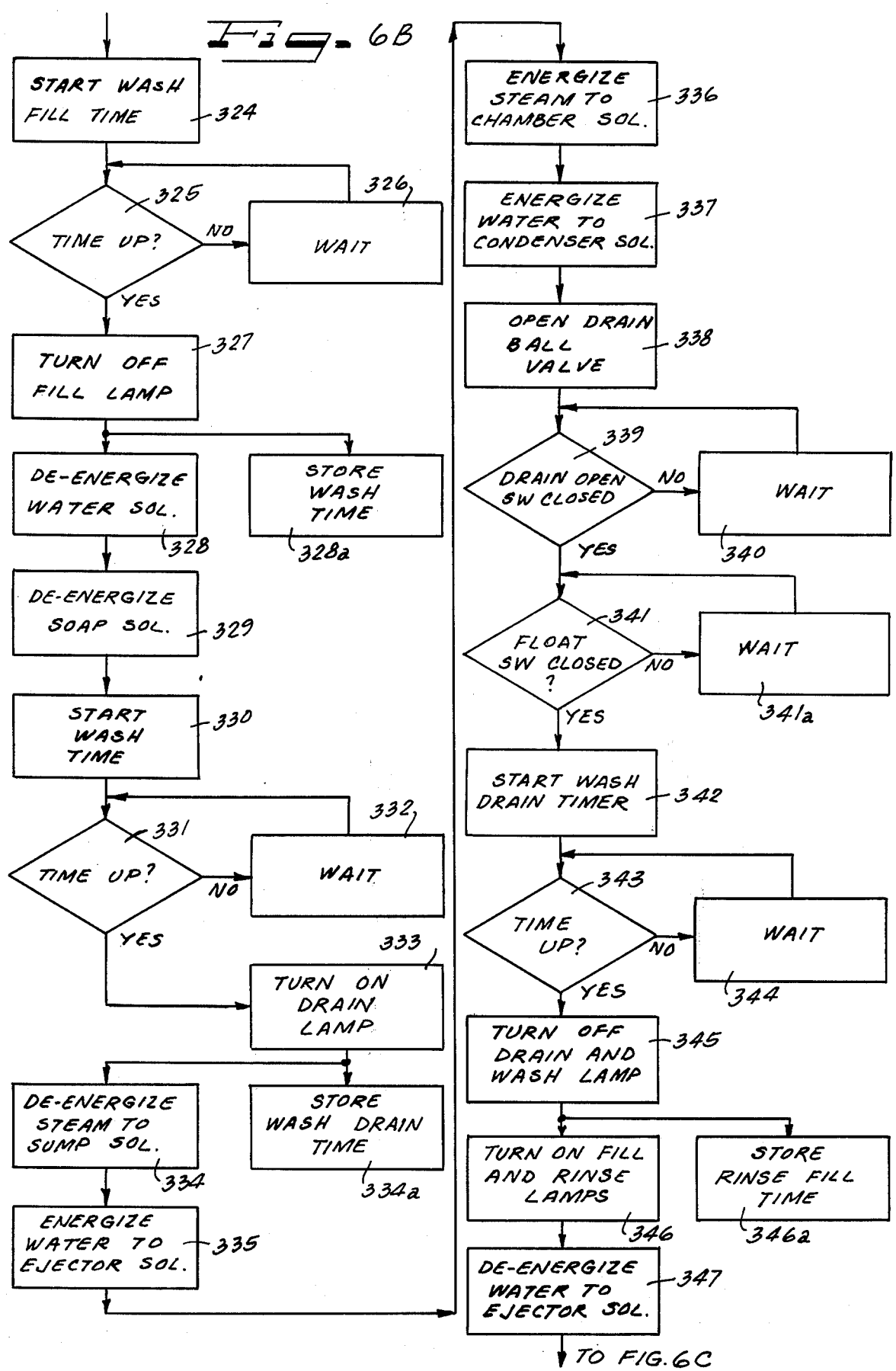

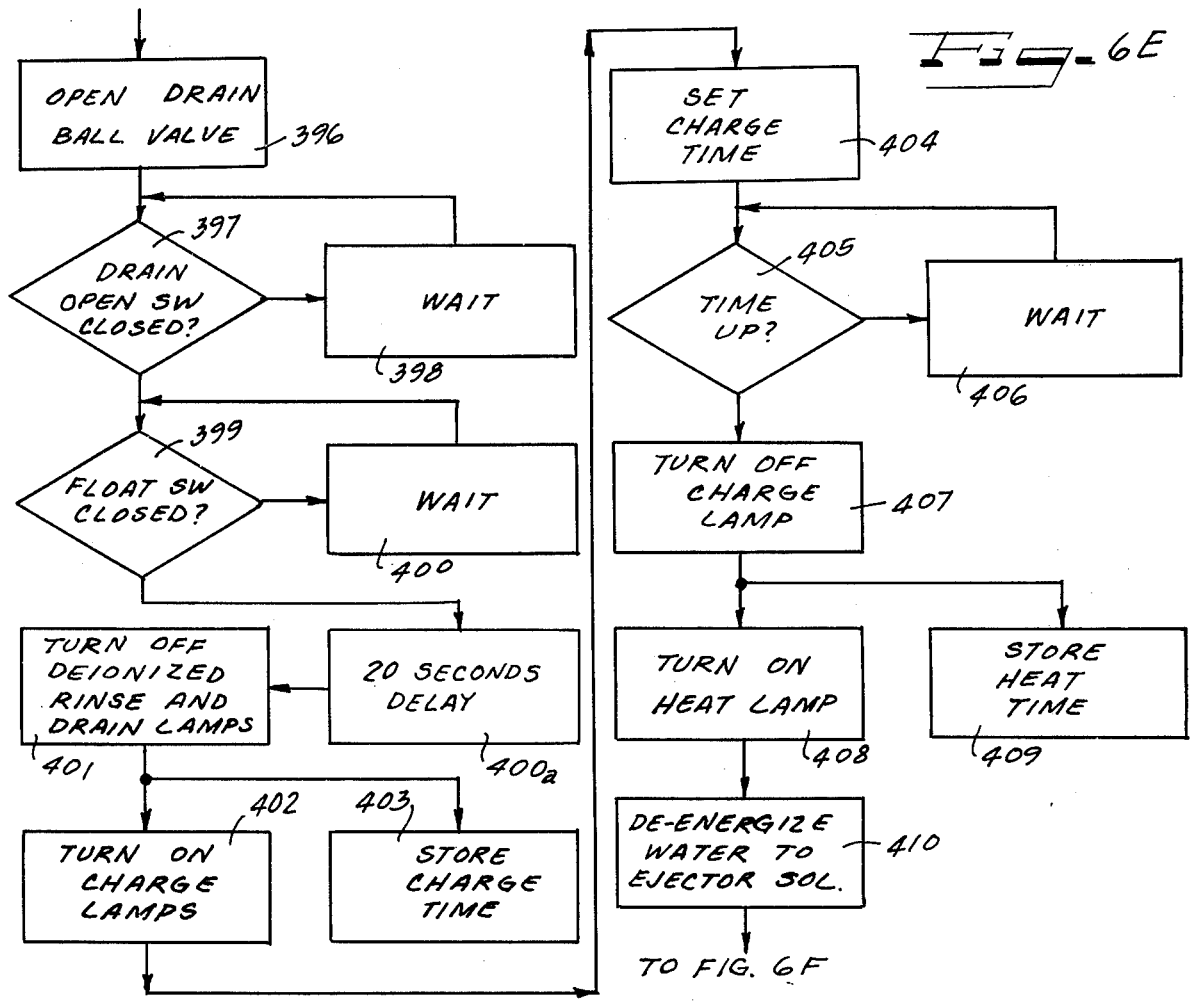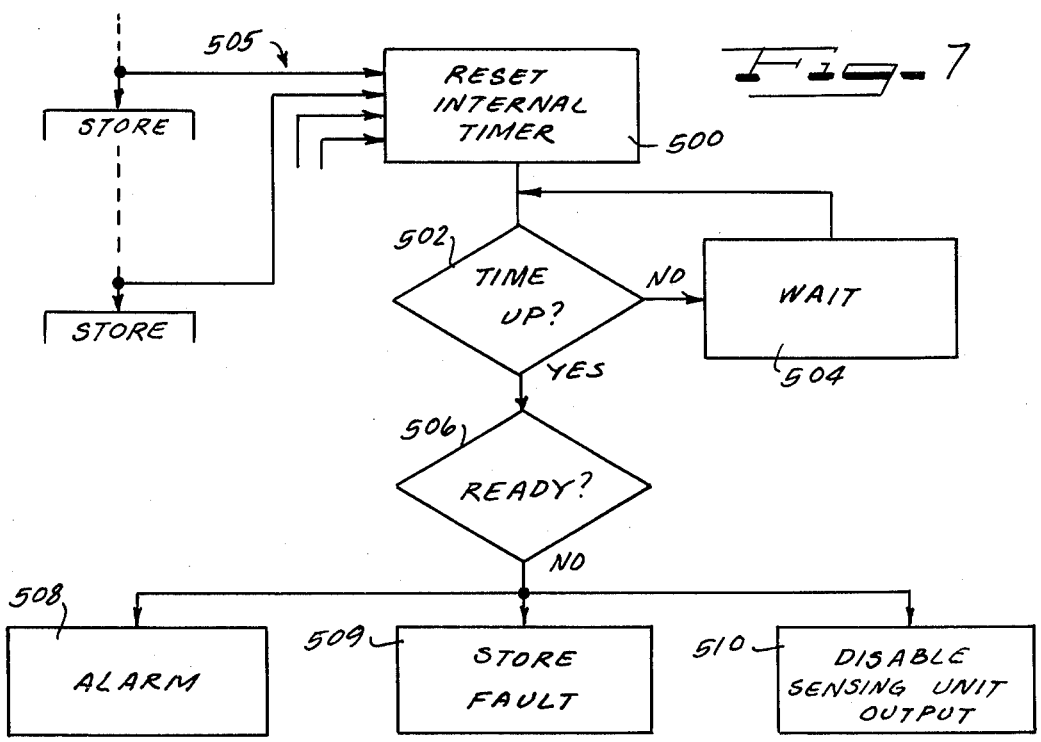

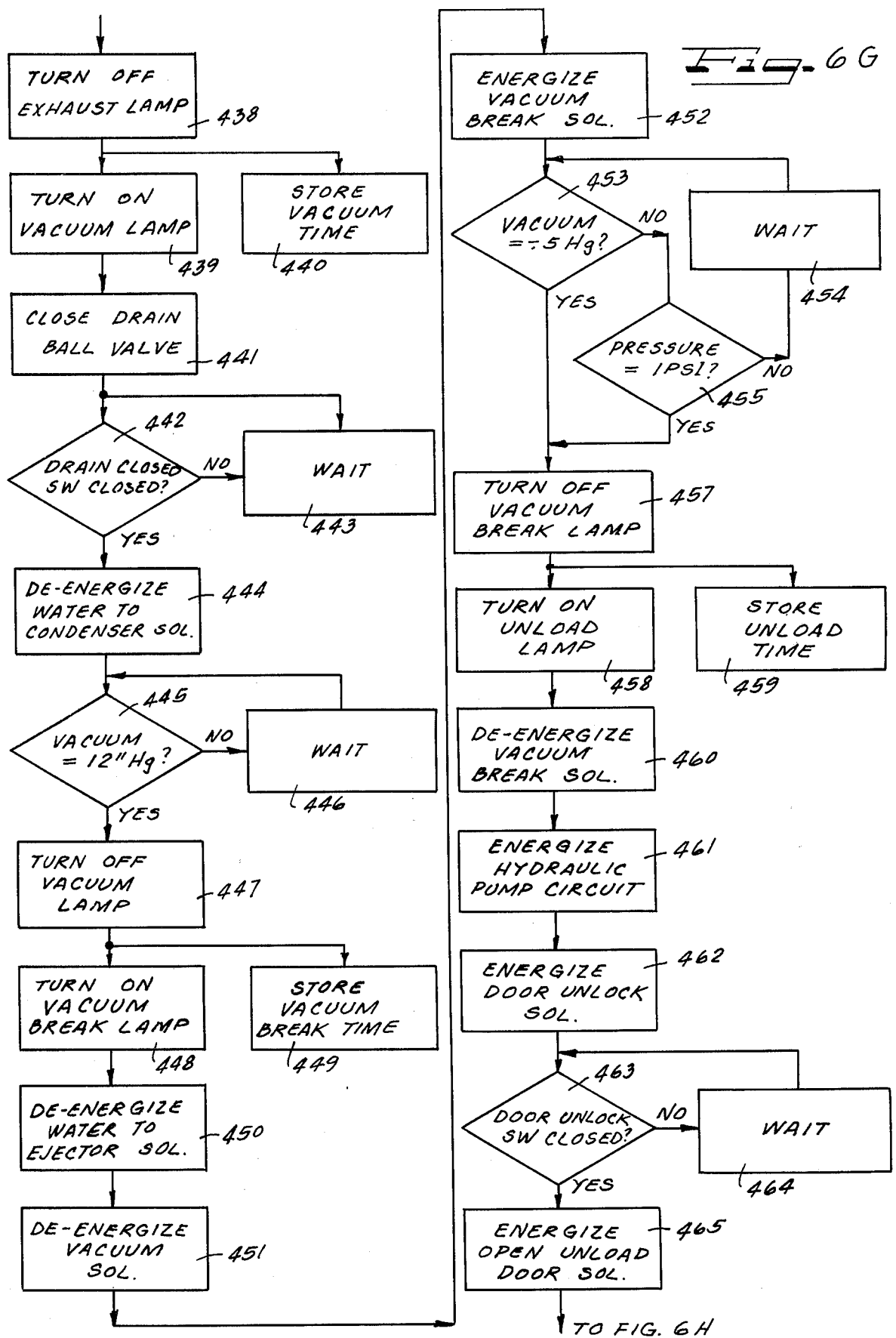

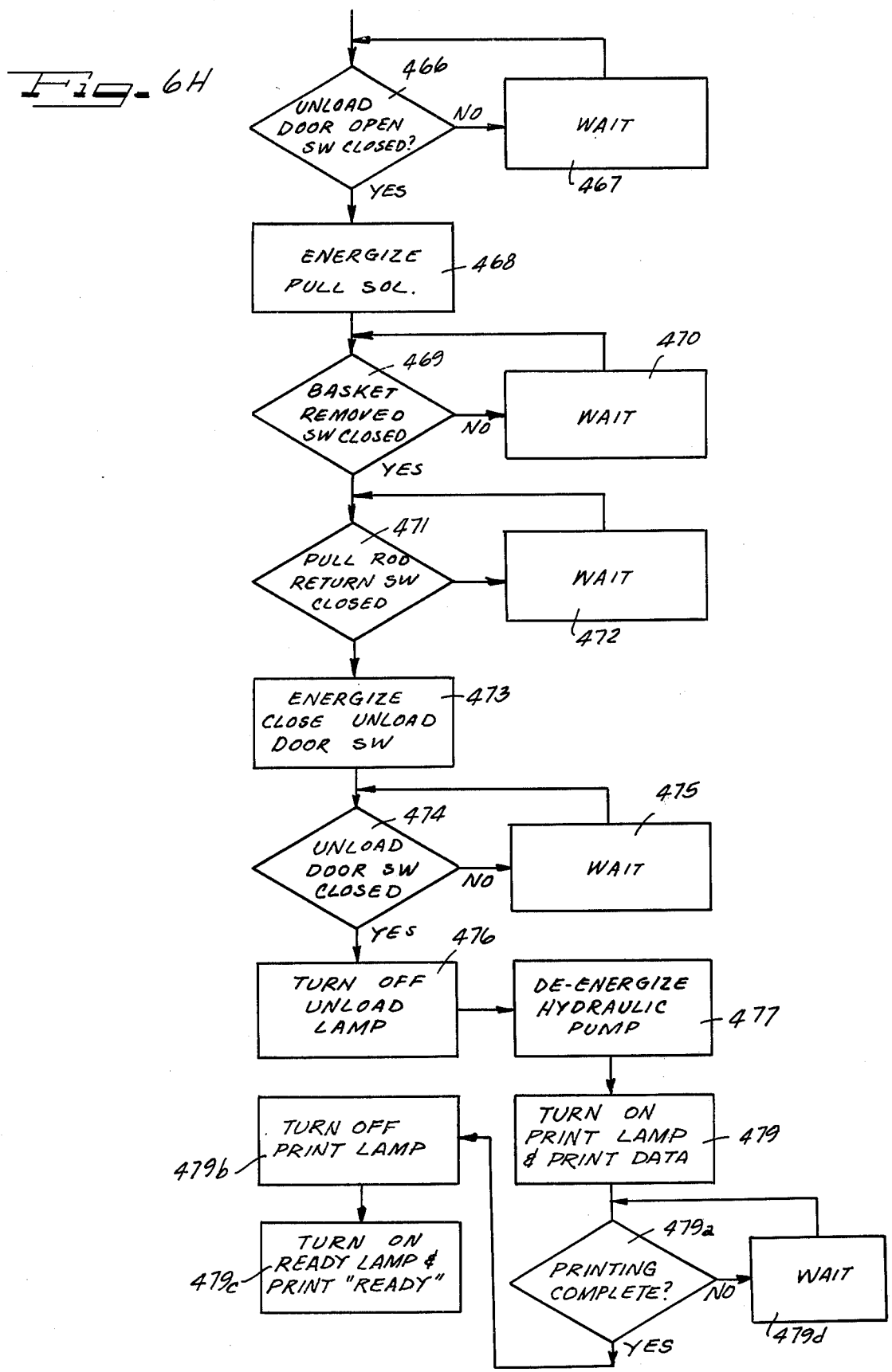

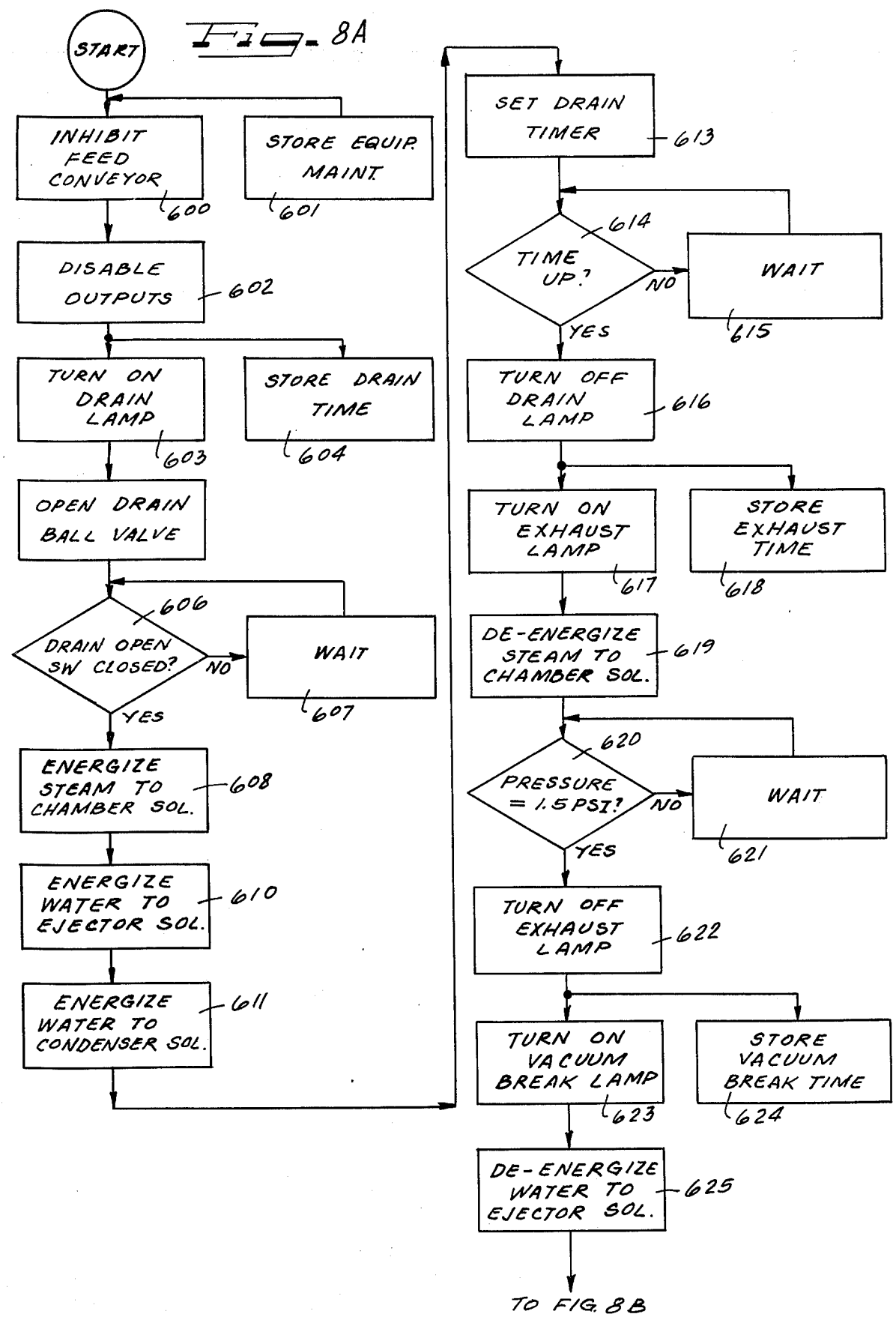

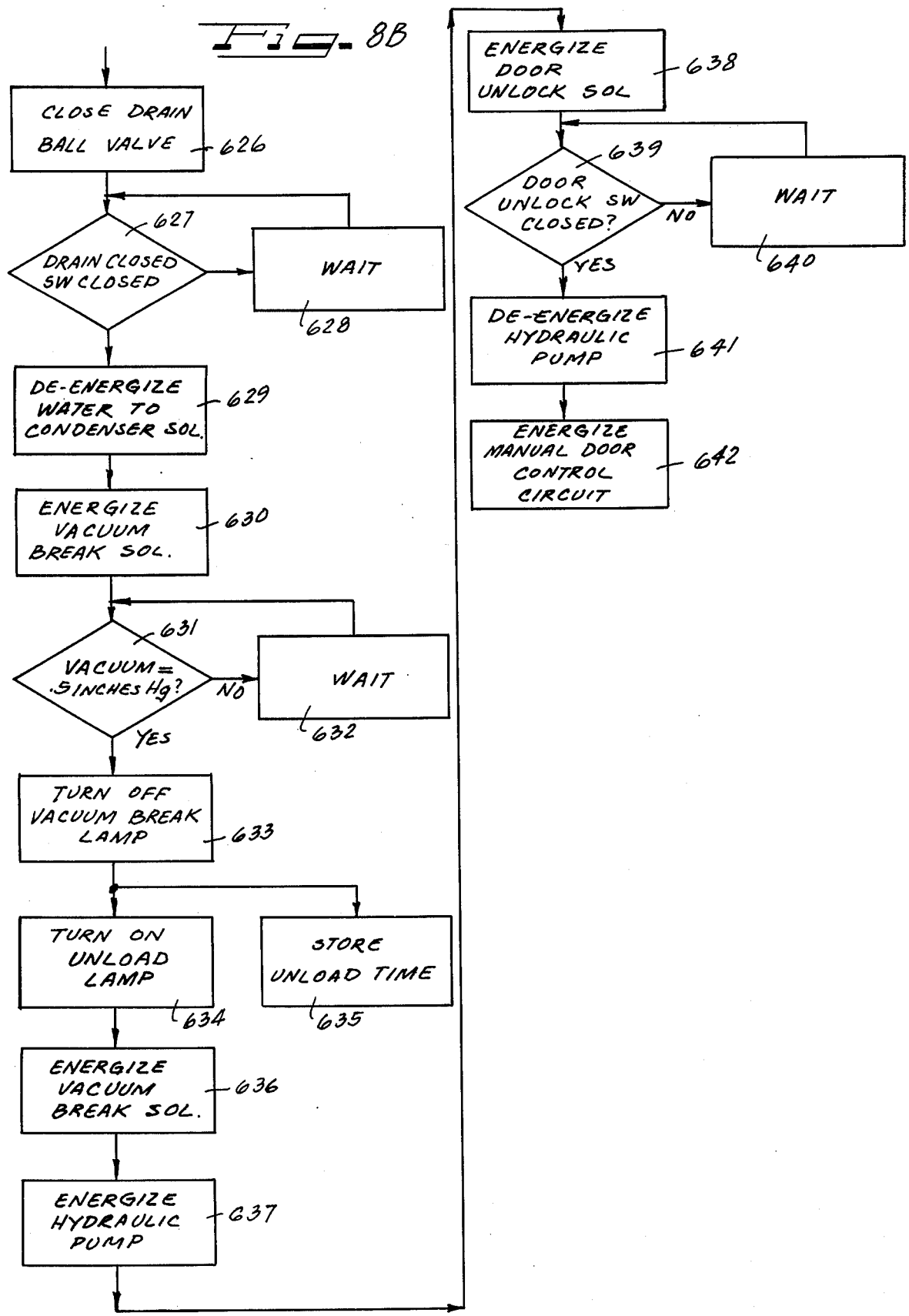

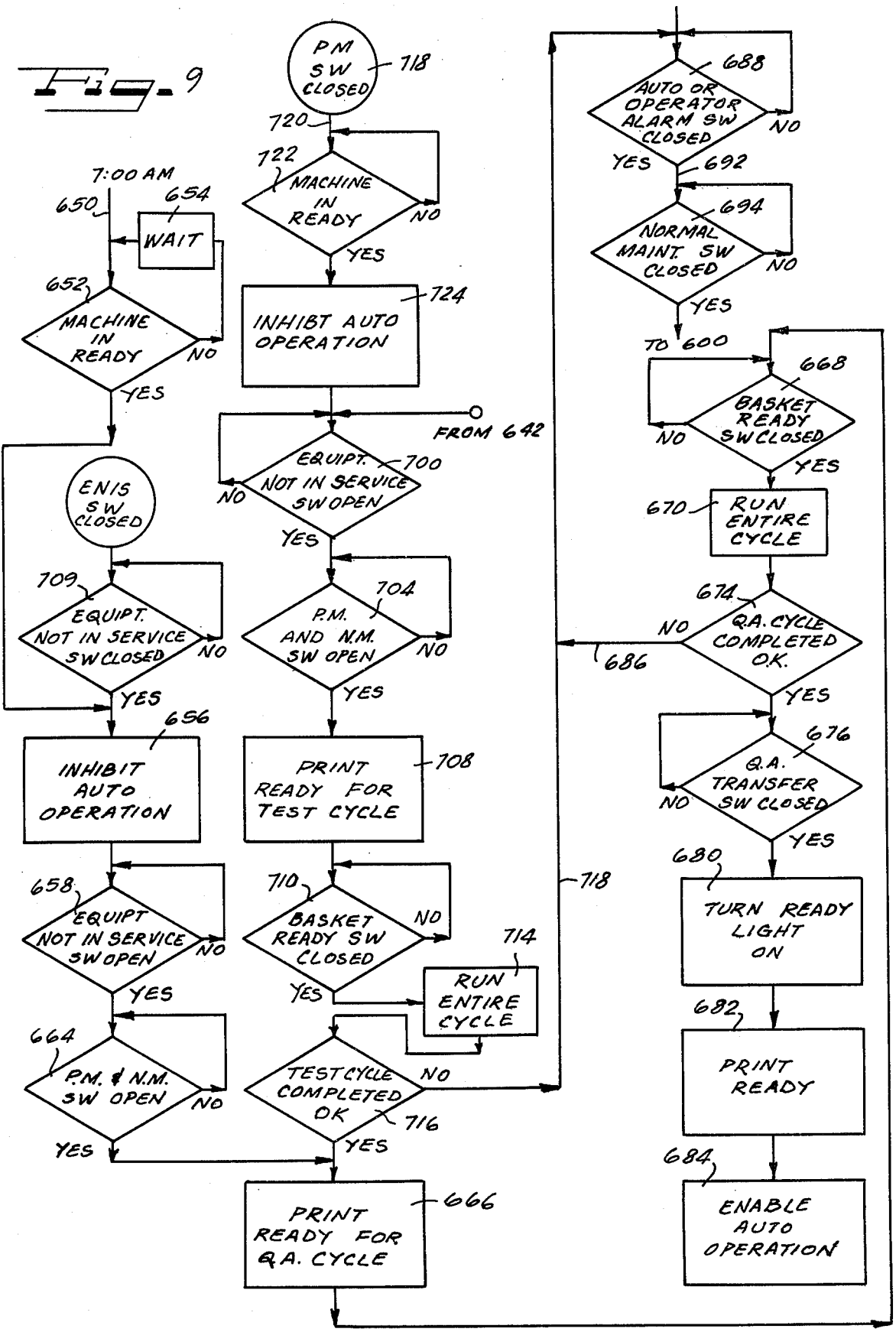

STERILIZING SYSTEM AND AUTOMATIC CONTROL THEREFOR

BACKGROUND

1. Field of the Invention

The present invention relates to sterilizing systems, and in particular to sterilizing systems as are used in hospitals for washing and sterilizing contaminated articles and implements before they are used in a clean environment in the hospital.

2. The Prior Art

Sterilizing systems for hospitals are well known, and are commonly relied on to safeguard patients and employees of hospitals from exposure to contamination. Typically, sterilizing machines are run on a semi-automatic basis, by being heated and pressurized in a given sequence of operations after being loaded with a quantity of articles to be sterilized. The machines are loaded from one side through an entrance door and unloaded in the opposite side through an exit door. The machines are installed in a wall separating a contaminated area from a clean area, where the sterilized implements and articles are typically assembled into packets for distribution throughout the hospital or where they are needed. Typically, a recording thermometer is associated with the sterilizing apparatus, and produces a chart record of the temperature within the sterilizing vessel during use.

Operation of the sterilizing apparatus is typically carried on by means of cam operated switches and cam operated valves, the cams being driven by a timer motor or the like. The operation of such apparatus is continuous, irrespective of the faulty operation during the sterilization process. For example, if during a step requiring a predetermined temperature or pressure, the temperature or pressure of the vessel does not increase to the prescribed point, the sterilization process remains incomplete and articles exiting from the exit opening of the sterilizing apparatus remain contaminated although presumed to be clean. The presence of the contaminated articles in the clean area may cause other articles, already sterilized, to become contaminated. Although reference to the chart record produced during operation of the apparatus may indicate, upon proper interpretation by a trained individual, the occurrence or non-occurrence of the prescribed steps of the sterilization procedure, such a determination can only be made upon a detailed inspection of each chart record, which is a relatively tedious process involving close scrutiny by a trained individual, and leaves considerable possibilities of human error resulting from non-reading or misreading of the chart.

When it is necessary to perform routine maintenance or repair on the sterilizing system, it is then necessary for a maintenance man to enter either the contaminated or the clean area in order to service the apparatus. In either case the maintenance man must be properly gowned with contamination resistant clothing, which interferes with his freedom of movement, and the presence of the maintenance man in either the contaminated or the clean area may interfere with the normal progress of activities in these areas. It is desirable, after maintenance procedures have been performed, to perform an equipment test cycle, to insure proper mechanical operation of the equipment, and then a quality assurance cycle, to insure that the equipment is performing its sterilizing function. In the prior art, however, there is no apparatus which prevents normal operation of the equipment before these procedures have been completed.

Accordingly, it is desirable to provide an apparatus and method for overcoming the disadvantages of the prior art systems.

SUMMARY OF THE INVENTION

It is a principal object of the present invention to provide a sterilizing system in which the components requiring access for maintenance are accessible in a neutral zone which is isolated from both the contaminated and the clean areas.

Another object of the present invention is to provide a sterilizing system in which maintenance personnel can service and/or repair the machine without being required to enter either a contaminated area or a clean area.

A further object of the present invention is to provide such apparatus in which a minimum of space is devoted to a neutral zone interposed between a contaminated area and a clean area.

Another object of the present invention is to provide a control system for a sterilizing apparatus which positively prevents completion of a cycle of operation of the apparatus and emission of articles into a clean area unless each step of the sterilization process is properly performed.

A further object of the present invention is to provide a control system for a sterilizing apparatus in which a printed record of the time and conditions of each sterilizing step is provided for future verification of the effectiveness of the sterilization procedure.

These and other objects of the present invention will become manifest by an inspection of the following description and the accompanying drawings.

In one embodiment of the present invention there is provided a sterilizing system comprising a vessel adapted to be heated and pressurized for carrying out a sterilizing process, an entry door for loading articles to be sterilized into the vessel from a contaminated area, an exit door for emitting sterilized articles into a clean area, and an isolated neutral zone defined by a first partition aligned with the entrance door and a second partition aligned with the exit door, a plurality of electrically operated controls for controlling the environment within the vessel, the controls being spaced above the vessel where they are accessible to a maintenance man, a plurality of sensing devices juxtaposed with said vessel for monitoring its condition, and a controller for supplying electrical signals to said electrically operated controls in response to predetermined signals from the sensing devices.

BRIEF DESCRIPTION OF THE DRAWINGS

Reference will now be made to the accompanying drawings in which:

FIG. 2 is an elevation of a portion of the apparatus illustrated in FIG. 1;

FIG. 3 is a functional block diagram of the major components of a sterilizing system constructed in accordance with an illustrative embodiment of the present invention;

FIG. 4 is a function block diagram of a plurality of sensing devices associated with a representative washer-sterilizer machine;

FIG. 5B is a schematic circuit diagram of a plurality of indicating lamps associated with the controller of the present invention;

FIGS. 6A-6H comprise a diagram illustrating operation of an automatic washer-sterilizer process;

FIG. 7 is a functional block diagram of a timer program for detecting a fault condition;

FIGS. 8A and 8B are diagrams illustrating maintenance and repair routines; and

FIG. 9 is a diagram illustrating the equipment test cycle routine and the quality assurance routine.

Referring now to FIG. 1, a plan view of a portion of a hospital floor is illustrated, in which three washer-sterilizer units 10, 12 and 14 are located. Each of the three sterilizer units 10, 12 and 14 has an entrance door opening in a wall 16, by which it communicates with a contaminated area 18. Each also has an exit door opening through a wall 20 by which it communicates with a clean area 22.

Figure 1:
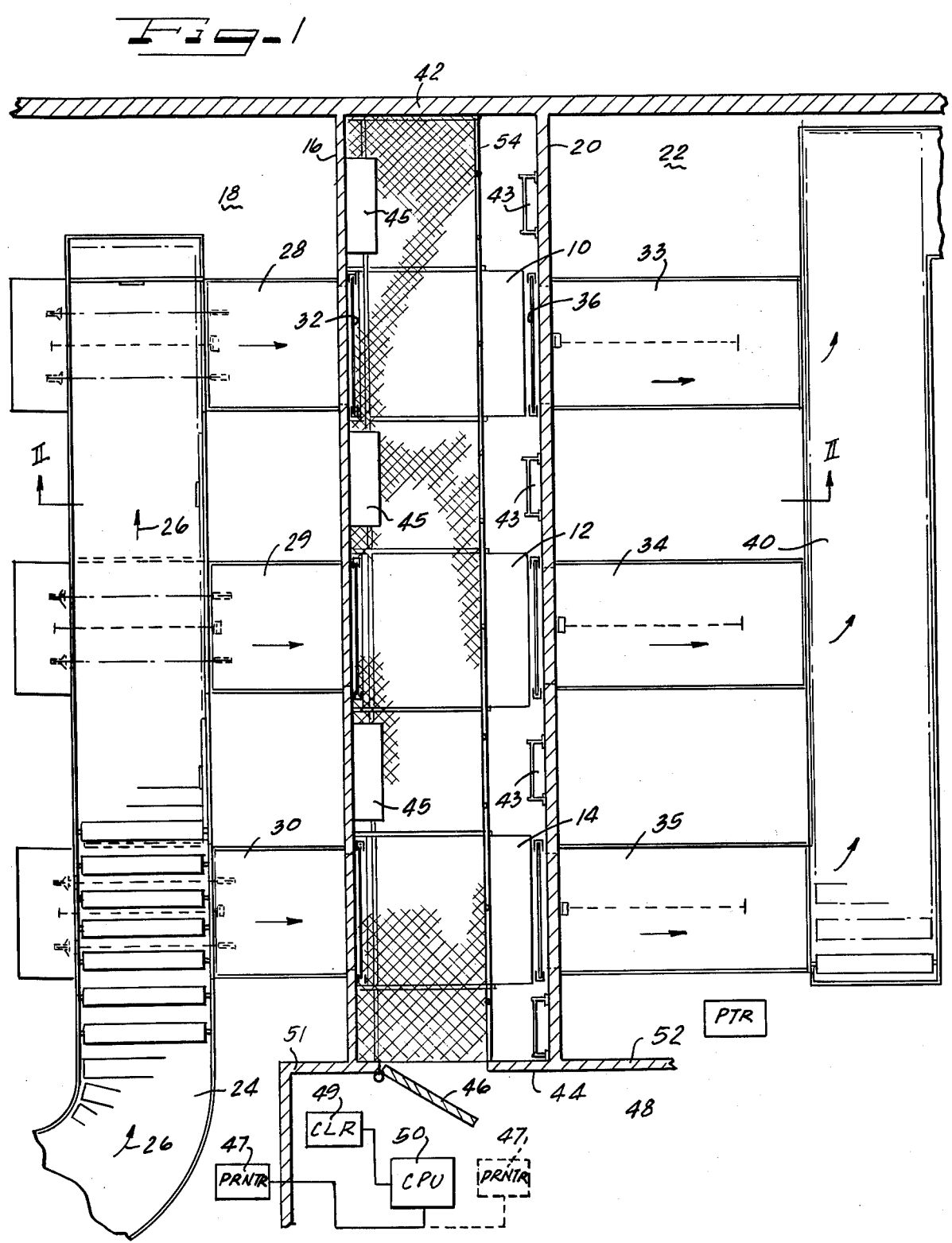
FIG. 1 is a plan view, partly in cross-section, of a sterilization area of a hospital, indicating the placement of sterilizing apparatus.

Contaminated articles arrive at the location of the sterilizer units 10, 12 and 14 by being carried by a transport conveyor 24. The conveyor 24 comprises a plurality of rollers for supporting a basket containing a quantity of articles to be sterilized. The rollers are rotated (by means not shown) so that the baskets are moved along the transport conveyor in the direction of the arrows 26. Three feed conveyors 28-30 are provided, one for each machine, by which baskets are moved into the three machines 10, 12 and 14. Baskets are transferred from the transport conveyor 24 to one of the three feed conveyors 28-30 (by means not shown) where they remain until conveyed into a washer-sterilizer machine at the beginning of a sterilization process.

Articles which have been sterilized pass from the machines 10, 12 and 14 to feed conveyors 33-35, respectively, and then to a transport conveyor 40. The conveyors 33-35 and 40 are all located in the clean area 22.

The washer-sterilizer 10 has an entrance door 32, which opens to admit a basket from the feed conveyor 28, and an exit door 36 which opens to allow a basket to be issued to the feed conveyor 33. The doors 32 and 36 are both maintained closed during a sterilizing process. The doors are opened one at a time, so the clean area and the contaminated area remain isolated from each other. Similar doors are provided for the other washer-sterilizer units 12 and 14.

The neutral zone between the walls 16 and 20 is sealed at one end by a wall 42 and at the other end by a wall 44 having a door 46. The door 46 opens the space between the walls 16 and 20 into a neutral area 48, which is separated by walls 51 and 52, respectively, from the contaminated area 18 and the clean area 22. The neutral area 48 is one in which employees and visitors can move freely without taking special precautions against being contaminated, or contaminating sterilized articles. All of the parts of the washer-sterilizer units 10, 12 and 14 which require maintenance are accessible within the closed neutral zone defined between the walls 16 and 20. The close side-by-side arrangement of the washer-sterilizer units 10, 12 and 14 permits maximum efficiency in the use of floor space in the area where the units are maintained. All of the electrically operated controls are located above the elevation of the main chamber of the sterilizer units 10, 12 and 14, where they are accessible to a maintenance man from a catwalk 54 which overlies the sterilizer units 10, 12 and 14, within the neutral zone defined between the walls 16 and 20. Boxes 45, shown mounted to the wall 16, are illustrative of the controls in FIG. 1. Ladders 43 are provided, secured to the wall 20, to allow a maintenance man to descend to the level of the sterilizing vessel, if necessary.

In the neutral area 48, a control system is located, which includes a controller unit 49 and a central processing unit or CPU 50. The central processing unit 50 has a printer 47 associated with it, for the purpose of printing out information received by the CPU 50 via the controller 49, originating with the various washer-sterilizer units 10, 12 and 14. The printer 47 is connected to the CPU 50 by means of a flexible cable or the like, so that it is movable. Normally, the printer is located in the contaminated area where it is accessible to an operator of the washer-sterilizer equipment. For maintenance procedures, however, it may be moved into the neutral area, as shown in dashed lines in FIG. 1.

FIG. 2, which is an elevational view, partly in cross-section through the washer-sterilizer unit 10, shows the relation of the feed conveyors 28 and 33 to the unit 10. The entrance and exit doors of the washer-sterilizer unit are mounted on tracks 32a and 36a, respectively, so that they open by sliding upwardly on their tracks. The catwalk 54 is located above the level of the unit 10, and the box 45 is readily accessible to a maintenance man standing on the catwalk 54. The box 45 is connected to sensing devices and to actuating devices 41a and 41b, associated with the unit 10, by lines indicated in FIG. 2 by dashed lines 41c and 41d. The box 45 is connected by lines 41e with the controller 49 and the CPU 50, and by lines 41f with a group of conduits 41g, including a source of electric power and pipes for supplying steam and water to the washer-sterilizer 10.

Referring now to FIG. 3 the general system for controlling the operation of three washer-sterilizers is illustrated. The three washer-sterilizers 10, 12 and 14 are each connected by several lines 51-53 to the controller 49. All of the signals transmitted and received by the controller 49 are digital in nature. The controller 49 is connected with the CPU 50 over a line 57. Analog signals generated in the washer-sterilizer unit 10 are converted into digital signals by means of an analog-to-digital converter 56, and the digital signals are transmitted to the central processing unit 50 over a line 58. Analog-to-digital converters 59 and 60 are also provided for the washer-sterilizer units 12 and 14, and they are also connected with the central processing unit for furnishing digital signals corresponding to analog signals generated by the washer-sterilizer unit. Digital signals are transmitted in both directions over the lines 51-57. It will be understood that each of the lines illustrated in FIG. 3 depicts a plurality of separate connections over separate wires.

The controller 49 has a memory unit 62 associated therewith, where the instruction sequence making up the program of operation is stored. The printer unit 47 which is associated with the CPU 50, furnishes a printed record of the operations involving the control of the washer-sterilizer units 10, 12 and 14. A timer unit 39, associated with the CPU 50 furnishes signals indicative of the time of day, so that the time when certain operations occur can be printed out by the printer 47.

The controller 49 is connected with an operator control panel 66, and a maintenance control panel 67. The operator control panel 66 is provided with a number of switches by which automatic operation of the washer-sterilizer units 10, 12 and 14 may be selected, and the control panel 67 has a number of switches for selecting maintenance operations and manual operations which are useful in connection with maintenance procedures. An indicator unit 68 is connected with the controller 49 and indicates the status of operation of the washer-sterilizer units. The control panel 66 and the indicator unit 68 may be located in the contaminated area, where they are accessible to an operator there, or in the neutral area adjacent the controller 49, or in the clean area, as desired.

Each of the washer-sterilizer units 10, 12 and 14 shown in FIG. 3 has a plurality of sensing devices associated therewith which produce signals in response to predetermined conditions during operation of the washer sterilizer units. In FIG. 4 the sensing devices for the unit 10 are illustrated in diagrammatic form.

All but three of the sensing devices of FIG. 4 are digital in nature and may therefore be referred to as switches. For example the drain-open switch 101 is normally open, but is closed when the drain of the sterilizing vessel is open. In like manner the drain-closed switch 102 is normally open, but is closed when the drain of the sterilizing vessel is closed. These switches furnish digital signals to the controller 49 over the line 51, during a program of operation of their respective washer sterilizer unit.

The switches 103-114 also furnish signals to the controller 49 over the line 51, in response to the occurrence of certain prescribed conditions. The switch 103 furnishes a signal when the water level within the sterilizing vessel is reduced to zero, as indicated by a float switch. A switch 104 produces a signal when a basket is ready, on the feed conveyor outside the washer sterilizer, to be inserted into the vessel for sterilizing. Switch 105 produces a signal when the push rod, which functions to load the basket into the sterilizing vessel, has returned to its retracted position after loading a basket into the sterilizing vessel. The switch 106 produces a signal when the pull rod, which is used for unloading a basket from the sterilizing vessel, has returned to its normal position outside the sterilizer vessel. A switch 107 produces a signal when a basket has been removed from the sterilizing vessel.

The switches 108—113 all indicate the condition of the load (entrance) door or the unloaded (exit) door. Switch 108 produces a signal when the load door is open; switch 109 produces a signal when the load door is closed; switch 110 produces a signal when the unload door is open; and switch 111 produces a signal when the unload door is closed. Switch 112 produces a signal when the load and unload doors are locked, and switch 113 produces a signal when the load door and the unload door are both unlocked. Switch 114 produces a signal when the hydraulic pressure has been increased to its operating value.

Switches 116 through 118 are all located on the control panel 66 and are operated by an operator. Preferably, they are the several positions of a single mode switch, by which the operator can choose the mode of the apparatus. Switch 116 is closed when the equipment is to be taken out of service and not available for automatic or manual operation. Switch 117 is closed by the operator if an alarm condition is to be signaled. Switch 118 is closed by the operator after a quality assurance cycle is completed. Preferably the switch 118 is operated by means of a key kept in the custody of a person of authority, so that it cannot be operated inadvertently by someone not authorized to do so.

The switches 119-121 are located on the maintenance control panel 67. Switch 119 is a preventive maintenance switch, which is closed by a maintenance man when preventive maintenance is to be performed on the unit. Switch 120 is closed when normal maintenance procedures are to be undertaken, and the switch 121 is closed when the doors of the washer-sterilizer unit are to be opened manually.

Units 122-124 are all analog sensors, and furnish analog signals to the analog-to-digital converters or ADC's 56, 59, 60. Either a separate ADC is employed for each analog signal, or the signals are multiplexed through a single ADC, as well understood in the art. The unit 122 senses the temperature in the range of from 0° to 300° F. The unit 123 senses the vacuum within the sterilizing vessel, and the unit 124 senses the steam pressure at a port of the sterilizing vessel. An analog-to-digital converter in each case converts the analog signal to digital information before passing it to the computer 50.

Figure 5A:
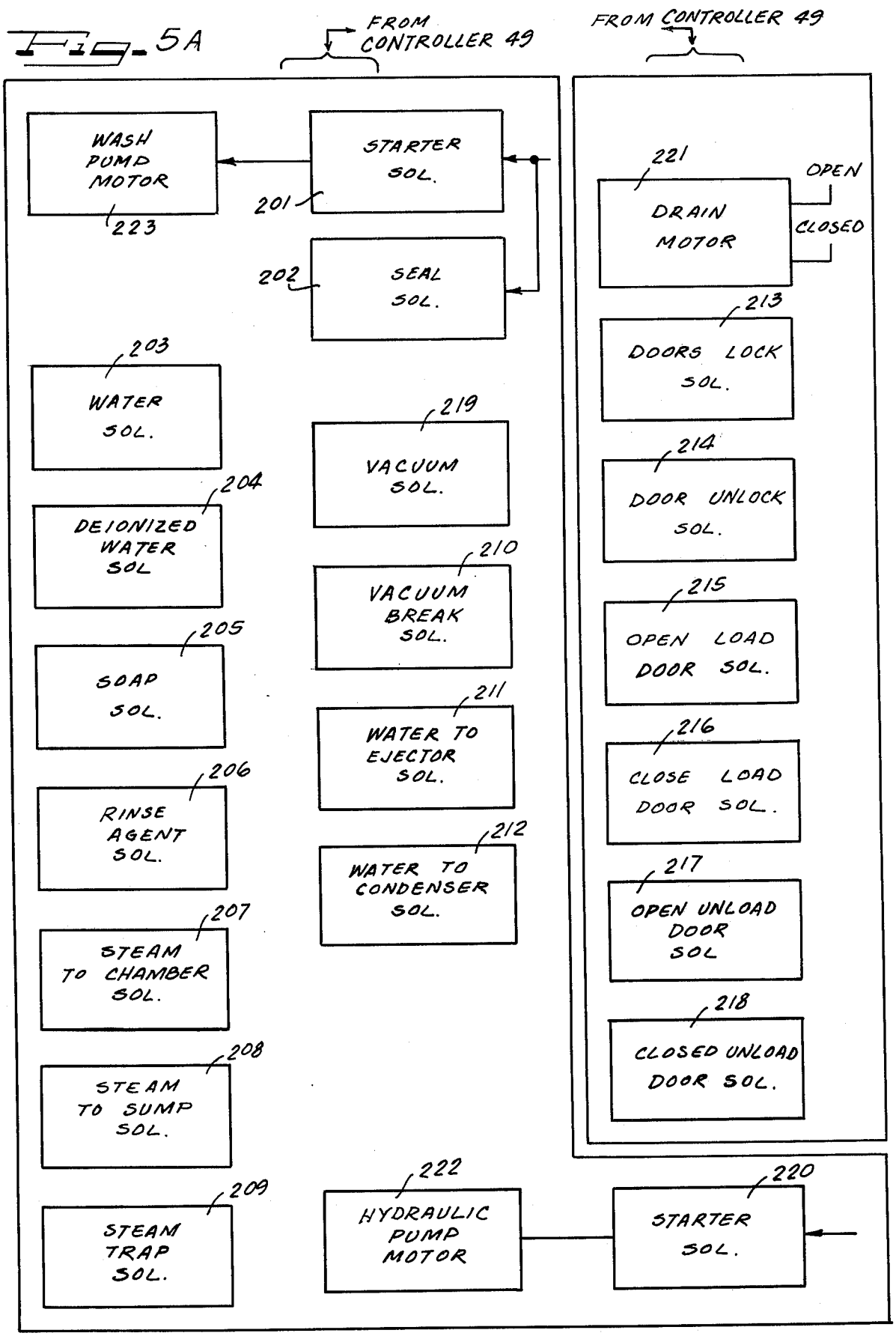
FIG. 5A is a functional block diagram of a plurality of electrically operated controls associated with a representative washer-sterilizer machine.
Figure 6A:
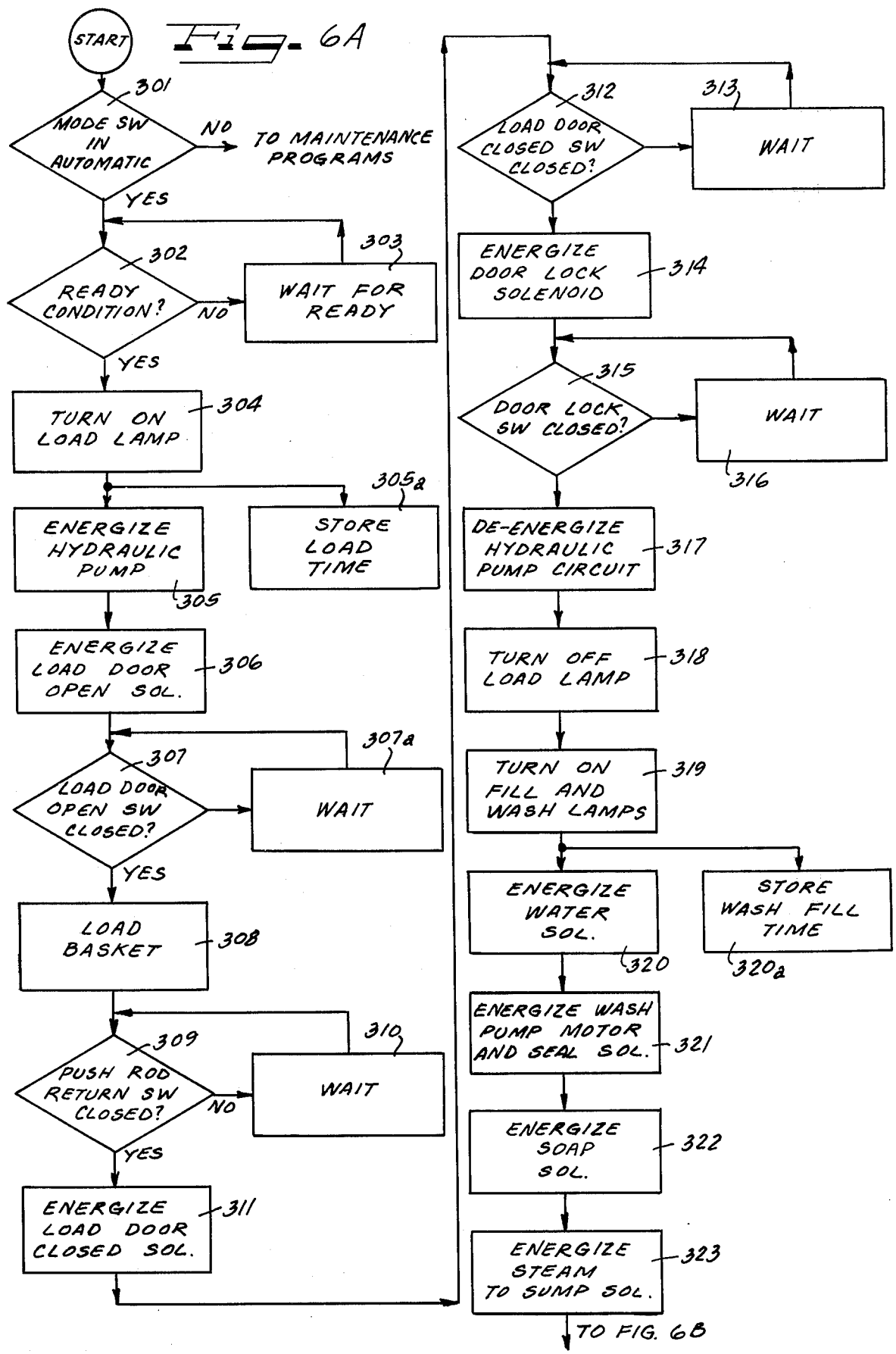
Figure 6C:
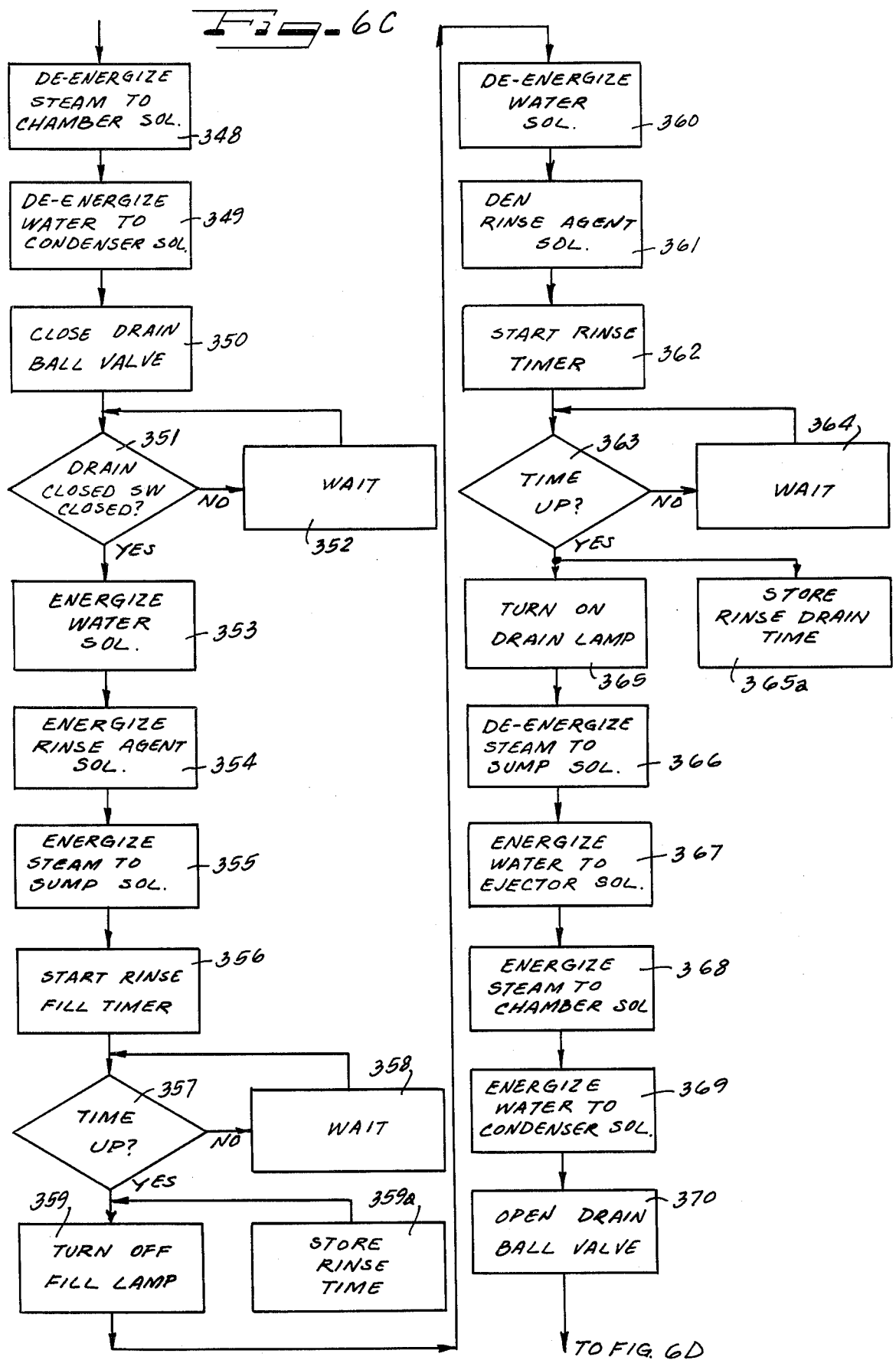
Figure 6D:
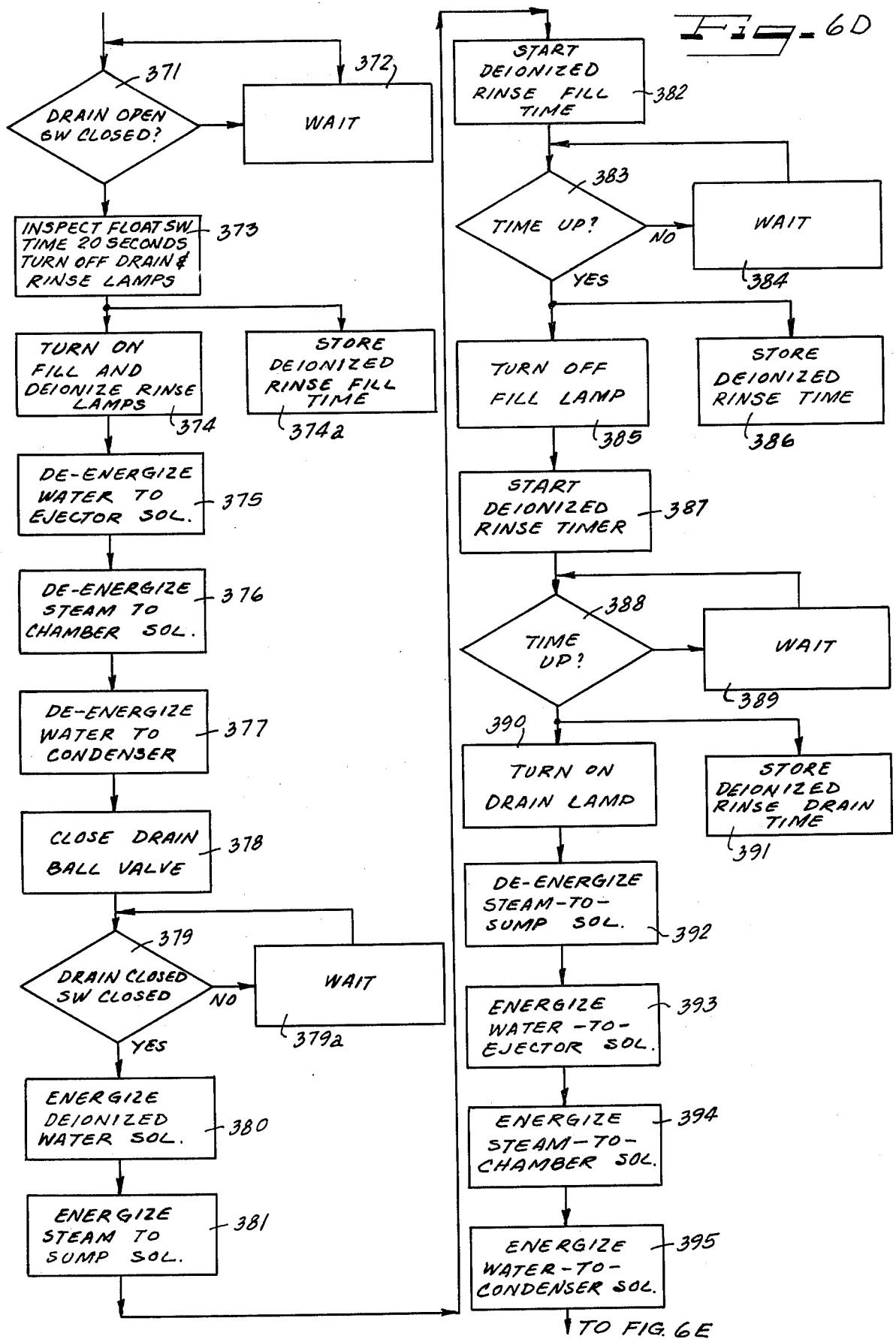
Figure 6F:
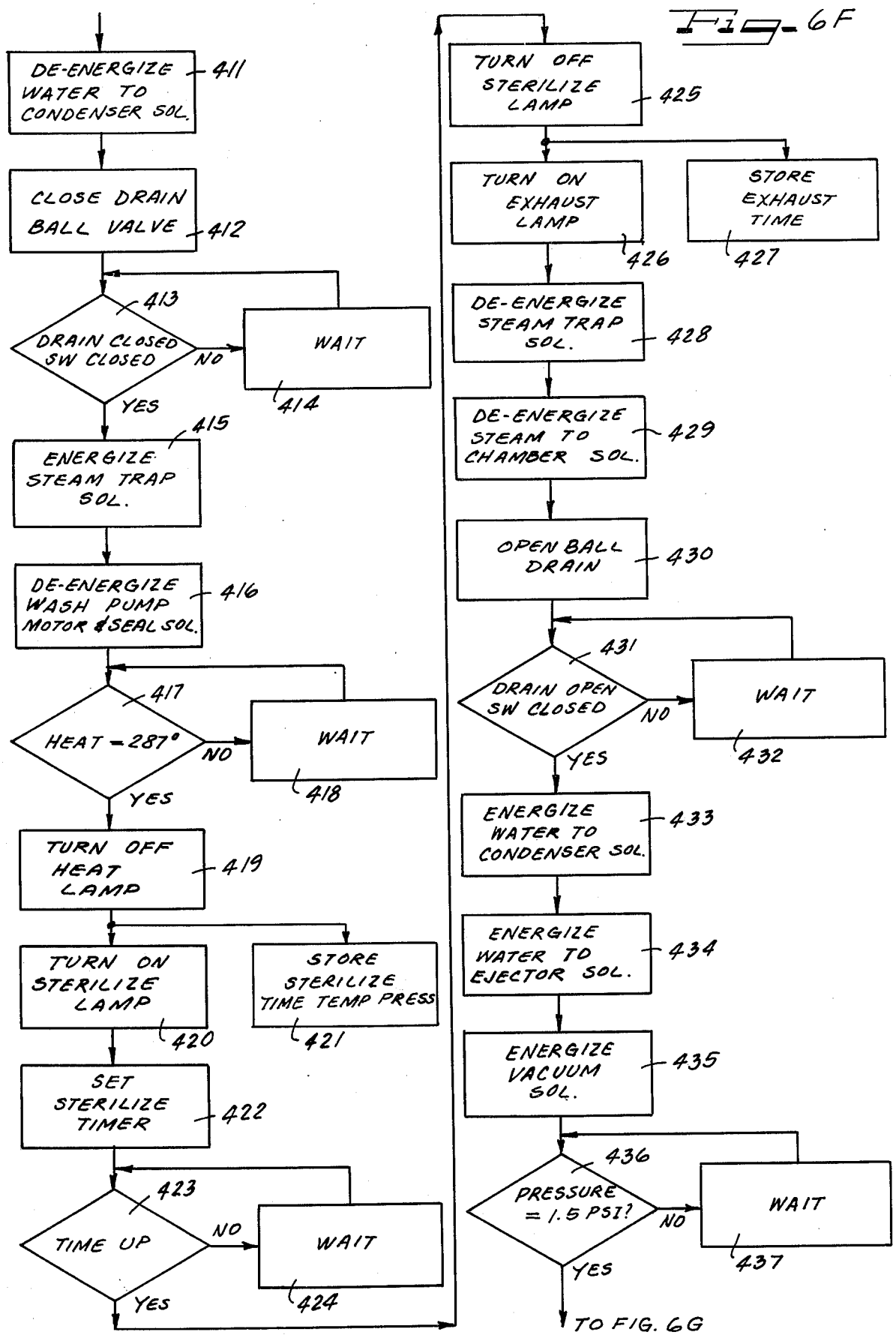

A plurality of controls are associated with each of the washer-sterilizer units 10, 12 and 14, for controlling the operation of the washer sterilizer units through a sterilizing program. The controls are solenoids and motors, which are capable of assuming an energized or a de-energized condition, in accordance with signals furnished to them from the controller 49. FIG. 5A shows the controls associated with the unit 10. The other units, of course, have an identical set of controls. The units 201-220 are all solenoids, for controlling operation of various devices within a washer-sterilizer unit.

Solenoids 201 and 202 are always energized and de-energized together, and control the starting of the motor 223 for driving the wash pump, and for effecting a seal whenever the pump motor is energized. Solenoid 203 is the water inlet solenoid, which controls a valve interposed between the water supply line and the sterilizing vessel. The solenoid 204 is the inlet solenoid for deionized water, and also controls a valve. Solenoid 205 is energized when soap solution is to be introduced into the vessel, and controls a valve interposed between the soap reservoir and the vessel. Solenoid 206 is energized in order to introduce a rinse agent into the vessel, and controls a valve interposed between a supply of rinse agent and the vessel. Solenoid 207 controls a valve for the introduction of steam into the vessel and solenoid 208 controls a valve in the path for the steam to the sump. Solenoid 209 is a steam trap solenoid, which controls operation of a valve associated with the steam trap. Solenoid 210 is the vacuum break solenoid which is energized when the vessel is to be brought to ambient pressure from a weak vacuum. The solenoid 211 controls a valve in the path of water flowing from the water supply to the ejector. Solenoid 212 controls a valve to regulate the flow of water into the condenser.

The solenoid 220 controls starting of the motor 222, which is run to build up hydraulic pressure when the doors are to be locked or unlocked, or when they are to be opened or closed. The starter solenoids 201 and 220 for the motors 222 and 223 are contained within the box 45, and are accessible to a maintenance man standing on the catwalk. Also, the electrical connection for the solenoids 201—212 and 220 are also located in the box 45.

Solenoids 213-218 are associated with the load (entrance) door and the unload (exit) door, and are positioned directly adjacent the washer-sterilizer unit 10. Solenoid 213 is the door lock solenoid which locks both the load door and unload door when energized. Solenoid 214 is the door unlock solenoid, which unlocks both doors when energized. Solenoid 215 is energized to open the load door; solenoid 216 is energized to close the load door; solenoid 217 is energized to open the unload door; and solenoid 218 is energized to close the unload door. Solenoid 219 is the vacuum solenoid, which is energized when a vacuum is desired in the sterilizing vessel. The drain valve motor 221 is also located adjacent the vessel, and is operative to open and close a valve in the drain line of the vessel.

The wash pump motor 223 runs in order to circulate water within the washer-sterilizer unit 10, and the hydraulic pump motor 222 runs only until the hydraulic pressure is high enough, as determined by the hydraulic pressure switch 114, to permit the opening and closing of the load door and the unload door.

A plurality of indicating lamps are shown in FIG. 5B, for indicating the state of operation of the washer sterilizer apparatus during a sequence of operations. These lamps may be located on the control panel 66, and/or placed in the contaminated area (or in the clean area if desired) where they are visible to an operator. All of the lamps 224-239 are illuminated by signals from the controller 49 in accordance with a program of operations. The ready lamp 224 is illuminated when the apparatus is ready to accept a basket of articles for sterilizing. The fill lamp 225 is illuminated to indicate that the vessel is being filled with water, and the lamps 226, 227 and 228 indicate the wash, drain and rinse cycles of the machine. Lamps 229 and 230 indicate the sterilization and the exhaust cycles of the machine. Lamp 231 is illuminated when the machine is in a vacuum condition; lamp 232 is illuminated during a deionized rinse; and lamp 233 is illuminated while the machine is being charged. Lamps 234 and 235 indicate the operation of the machine during the load and unload procedures. The lamp 236 is illuminated when the vacuum is being broken, and the lamp 237 is illuminated during the heat cycle. Lamp 238 is illuminated to indicate that the quality assurance cycle is running, and the lamp 239 is illuminated during maintenance procedures.

FIGS. 6A-6H illustrate the operation of the apparatus of the present invention during an automatic cycle of operation. FIG. 6 is a functional block diagram form, with the various blocks indicating steps performed in sequence during the performance of the method of the present invention, and also indicating the structure which is employed during the operation of the washer-sterilizer machine. Although a preferred embodiment of the present invention employs a controller for the performance of the sterilizing program, the present invention also contemplates an organization in which each of the blocks illustrated in FIG. 6 corresponds to an individual control unit. Control of the operation is passed from control unit to control unit, to execute the program in its proper sequence. The operation proceeds by a sequence of steps, and successful completion of some of the steps is signaled by the closing of one of the switches illustrated in FIG. 4. Where it is necessary to verify that a prescribed operation has occurred (for examle, the locking of the load door before the wash pump motor is energized) the apparatus enters a wait state, in which it waits for the prescribed signal. The subsequent control unit does not receive control until after the appropriate signal has been received, verifying completion of the previous operation.

The first step in the performance of the automatic operation of the washer-sterilizer is by control unit 301 to inspect the mode switch (viz, the switches 116-118) to determine whether it is in its automatic setting, corresponding to a state in which none of the switches 116-118 are closed. The switches 119 and 120 must also be unoperated, for the apparatus to operate in an automatic mode. If all of the switches 116-120 are open, control passes to a unit 302 which examines the status of other sensing devices shown in FIG. 4, to determine whether the sterilizing vessel is ready to have its load door opened to receive a basket from the feed conveyor. If not, control passes to a unit 303 which introduces a delay and returns control to the unit 302 repeatedly until the ready condition is sensed. The unit 303 may be a simple delay device, but preferably branches control to an executive routine of the controller 49, which can then perform other programs during the period of the delay, after which control is returned to unit 302. The units 301 and 302 are preferably comparators, able to compare two sets of data, and branch to one of two different control units in response to the result of the comparison. One set of data originates with the sensing devices of FIG. 4, with the second set being derived from the memory unit 62, where it is permanently stored. Alternatively, the second set of data is hard wired to the comparator. As these techniques are well known to those skilled in the art, they need not be described in detail.

In the subsequent operations which occur in connection with the operation of the washer-sterilizer, a number of wait units are employed, to cause the apparatus to wait until a prescribed signal has been received from a sensing device. In each of these instances control may be passed to an executive routine instead of making the controller 49 wait idly for the necessary signal.

When the ready condition is sensed by the control unit 302, control is passed to a unit 304 which turns on the load lamp 234, which then visually indicates that the load cycle is being performed. Control then passes to a unit 305 which energizes the hydraulic pump circuit by way of starter solenoid 220 (FIG. 5), and to a unit 305a which causes the CPU 50 to store, in its memory, an indication that the load cycle has started, and the current time of day (from the timing device 39). The pump operates for a period of 12 seconds, after which the starter solenoid 220 is de-energized. The starter solenoid 220 is re-energized automatically when the hydraulic pressure switch 114 indicates that the hydraulic pressure has fallen below a given level. This sequence establishes the required pressure in the hydraulic lines to open and close and for locking the doors of the sterilizing vessel.

Control is passed from the unit 305 to the unit 306 which energizes the load door-open-solenoid, after which control is passed to the unit 307 which inspects the load door-open-switch. While the switch remains open, control is passed to the wait unit 307a which re-enters the unit 307 repeatedly until the door-open-switch is found closed, indicating that the load door is fully opened. Control is then passed to the unit 308 which controls a push rod to load a basket from the feed conveyor into the vessel, and control is passed to unit 309 which inspects the push rod return-switch 105, which is closed when the push rod (which enters the basket into the vessel) has returned to its normal position. Until it does so a wait unit 310 repeatedly returns control to the unit 309 until the push rod return-switch is closed. Then control passes to the unit 311 which energizes the load door-closed solenoid 216. The unit 312 then inspects the load door-closed-switch and passes control to a wait unit 313 until the switch is found closed, after which control passes to the unit 314 which energizes the door-lock-solenoid 213. The unit 315 then inspects the door-lock-switch, and passes control to a wait unit 316 until the switch is found closed, after which control is passed to the unit 317 for de-energizing the hydraulic pump circuit, since the hydraulic pressure is not required during operation of the washer-sterilizer unit except for opening and closing the doors, and for locking them.

When the hydraulic pump circuit has been de-energized control passes through a succession of units 318–320, 320a and 321–324 which function respectively to turn off the load lamp, turn on the fill and wash lamps, energize the water solenoid 203, store in the internal memory unit of the CPU 50 the time and occurrence of the wash fill cycle, energize the wash pump-motor and starter solenoid 201 and the seal solenoid 202, energize the soap solenoid 205, energize the steam-to-sump-solenoid 208, and start the wash-fill-timer.

The wash-fill-timer may be either a separate timer unit 39 (FIG. 3), or a timing program executed by the controller 49. In either event, the timer is set for a time of 25 seconds, and control unit 325 repeatedly examines the timer to determine when the time is up. Control is passed to wait unit 326 until the 25 second period of the wash fill cycle expires, after which control is passed to a succession of units 327–330, which function to turn off the fill lamp, de-energize the water solenoid, de-energize the soap solenoid, and start the wash timer. Unit 328a, which operates concurrently with unit 328, stores the current time of day, to record the time the wash cycle started.

The wash cycle is preferably 5 minutes in length, and so the wash timer, which may be either a separate unit or a timing program executed by the controller 49, is set for a time of 5 minutes. The unit 331 examines the timer and passes control to the wait unit 332 unit the 5 minute period is up, after which control is passed to a succession of units 333, 334, 334a and 335–338. These units fuction respectively to turn on the drain light, de-energize the steam-to-pump solenoid, store in the CPU memory the time of day to record the time the wash drain cycle started, energize the water-to-ejector solenoid, energize the steam-to-chamber solenoid, energize the water-to-condenser solenoid, and open the drain ball valve. The drain ball valve is controlled by a drain motor 221 (FIG. 5A) which is energized to open and close the drain.

Control is then passed to the unit 339 which inspects the state of the drain-open switch. Control is passed to a wait unit 340 until the switch is closed, after which control is passed to the unit 341. The unit 341 inspects the status of the float switch 103. If it is closed, indicating that all of the water has passed down the drain, control passes to the next unit 342. Otherwise control passes to a wait unit 341a until the switch is found to be closed.

The unit 342 then sets the wash drain timer to 20 seconds.

Unit 343 inspects the timer to determine when the time is up and passes control to a wait unit 344 until the 20 second period has expired.

The unit 345 turns off the drain and wash lamps, then the unit 346 turns on the fill and rinse lamps, and the unit 346a stores in the CPU 50 memory the current time of day, e.g. the rinse-fill time. Then the unit 347 de-energizes the water-to-ejector solenoid, the unit 348 de-energizes the steam-to-chamber solenoid, the unit 349 de-energizes the water-to-condenser solenoid, and the unit 350 closes the drain valve. The unit 351 inspects the drain-closed switch and passes control to a wait unit 352 until the switch is found to be closed, after which control is passed to a succession of units 353–356. Unit 353 energizes the water solenoid, unit 354 energizes the rinse agent solenoid, unit 355 energizes the steam-to-sump solenoid, and the other 356 starts the rinse fill timer. The rinse fill cycle is 25 seconds in length.

The unit 357 examines the timer to determine when the time is up and passes control to a wait unit 358 until the time expires, after which control is passed to unit 359 which turns off the fill lamp, and a unit 359a which stores in the CPU memory the rinse time.

Then a unit 360 de-energizes the water solenoid; a unit 361 de-energizes the rinse agent solenoid; and a unit 362 starts the rinse timer. The rinse period is typically 1 minute in length and so the timer is set to a period of 1 minute.

The unit 363 examines the state of the timer and passes control to a wait unit 364 until the time is up, after which the unit 365 turns on the drain lamp, the unit 365a stores the rinse drain time, the unit 366 de-energizes the steam-to-sump solenoid, the unit 367 energizes the water-to-ejector solenoid, the unit 368 energizes the steam-to-chamber solenoid, the unit 369 energizes the water-to-condenser solenoid, and the unit 370 opens the drain valve. The unit 371 inspects the drain-open switch and passes control to a wait unit 372 until the switch is found closed, after which the unit 373 inspects the float switch, introduces a delay of 20 seconds after the float which is closed, and turns off the drain and rinse lamps. The unit 373 incorporate the units 341–343 shown separately in FIG. 6B for the first two functions. Then the unit 374 turns on the fill and deionized rinse lamps. The unit 374a stores the deionized rinse fill time.

The unit 375 de-energizes the water-to-ejector solenoid, the unit 376 de-energizes the steam-to-chamber solenoid, the unit 377 de-energizes the water-to-condenser solenoid, and the unit 378 closes the drain valve. The unit 379 inspects the status of the drain-closed switch and passes control to the wait unit 380 until the switch is closed.

When the drain-closed switch is closed, the unit 380 energizes the deionized water solenoid, the unit 381 energizes the steam-to-sump solenoid, and the unit 382 starts the deionized rinse fill timer. The deionized rinse fill cycle is typically 25 seconds. The unit 383 inspects the state of the timer and passes control to the wait unit 384 until the time is up, after which the unit 385 turns off the fill lamp and the unit 386 stores deionized rinse time. Then the unit 387 starts the deionized rinse timer. This cycle takes 1 minute, and so the timer is set to 1 minute.

The unit 388 examines the rinse timer and passes control to a wait unit 389 until the 1 minute time is up. Then the unit 390 turns on the drain lamp and the unit 391 stores the deionized rinse drain time.

Control then passes to a succession of units 392–397 which de-energize the steam-to-sump solenoid, energize the water-to-ejector solenoid, energize the steam-to-chamber solenoid, energize the water-to-condenser solenoid, open the drain ball valve and inspect the state of the drain-closed switch. Control passes to a wait unit 398 until the switch is found to be closed, after which control passes to the unit 399 which inspects the status of the float switch and passes control to a wait unit 400 until the float switch indicates that all of the water has been drained from the vessel. Then a unit 400a introduces a twenty second time delay. The unit 400a includes the unit 342–344 shown separately in FIG. 6B. Then the unit 401 turns off the deionized rinse and drain lamps, the unit 402 turns on the charge lamps, and the unit 403 stores the charge time. The charge timer is set by the unit 404 typically to a time of 20 seconds, and the unit 405 examines the state of the timer to determine when the time has expired, passing control to a wait unit 406 until the 20 second period has elapsed.

The unit 407 turns off the charge lamp, the unit 408 turns on the heat lamp, the unit 409 stores the heat time, the unit 410 de-energizes the water-to-ejector solenoid, the unit 411 de-energizes the water-to-condenser solenoid, and the unit 412 closes the drain valve. The unit 413 inspects the drain-closed switch and passes control to a wait unit 414 until the switch is closed. Then unit 415 energizes the steam strap solenoid; and the unit 416 de-energizes the wash pump motor and the seal solenoid. Unit 417 then inspects the signal from the heat sensor 121 and passes control to a wait unit 418 until the heat sensor 121 indicates that the heat has reached 287°. Then control is passed to a unit 419 which turns off the heat lamp. The unit 420 turns on the sterilize lamp, the unit 421 stores the sterilize time, along with representations of the temperature and pressure at that time, and the unit 422 sets the sterilizer timer. The sterilize cycle is typically thirty seconds and so the sterilizer timer is set for 30 seconds.

The unit 423 examines the timer to determine when the time is up, passing control to a wait unit 424 until the time has expired. Then the unit 425 turns off the sterilize lamp, the unit 426 turns on the exhaust lamp, and the unit 427 stores the exhaust time. Then unit 428 de-energizes the steam trap solenoid, the unit 429 de-energizes the steam-to-chamber solenoid and the unit 430 opens the drain. The unit 431 inspects the drain open switch and passes control to a wait unit 432 until the switch is closed. The unit 433 energizes the water-to-condenser solenoid, the unit 434 energizes the water-to-ejector solenoid, and the unit 435 energizes the vacuum solenoid. The unit 436 then inspects the output of the vacuum sensor 122 until the pressure equals 1½ pounds per square inch, passing control to the wait unit 437 until the pressure reaches that value. Then the unit 438 turns off the exhaust lamp, the unit 439 turns on the vacuum lamp, the unit 440 stores the vacuum time, and the unit 441 closes the drain. Unit 442 inspects the drain-closed switch and passes control to a wait unit 443 until the switch is found closed.

When the unit 442 finds the drain-closed switch closed, it passes control to the unit 444 which de-energizes the water-to-condenser solenoid and passes control to unit 445 which inspects the signal produced by the vacuum sensor 122. When the vacuum sensor produces a signal corresponding to 12 inches of mercury, it passes control to a unit 447. Otherwise it passes control to a wait unit 446 which returns control to the unit 445 until the correct vacuum signal is sensed.

The unit 447 turns off the vacuum lamp, the unit 448 turns on the vacuum-break lamp, and the unit 449 stores the vacuum-break time. Then the unit 450 de-energizes the water-to-ejector solenoid; the unit 451 de-energizes the vacuum solenoid and the unit 452 energizes the vacuum-break solenoid. Control then passes through unit 453 which inspects the output of the vacuum sensor 122. If the vacuum is not equal to one-half an inch of mercury, control passes to a unit 455 which examines the output of the pressure sensor 123. If the pressure is equal to 1 p.s.i., control is passed to a unit 457. Otherwise, control is passed to a wait unit 454, which returns control to the unit 453. When the unit 453 senses that the vacuum is equal to one-half inch of mercury, control passes directly to the unit 457. In this way, the unit 457 receives control as long as the pressure is almost atmospheric, so that it is safe to open the door.

The unit 457 turns off the vacuum break lamp; the unit 458 turns on the unload lamp; the unit 459 stores the unload time; the unit 460 de-energizes the vacuum break solenoid; the unit 461 energizes the hydraulic pump circuit; and the unit 462 energizes the door unlock solenoid.

Then unit 463 inspects the status of the door unlock switch, passing control to a wait unit 464 until the door unlock switch is closed. Then control passes to a unit 465 which energizes the open unload door solenoid, after which unit 466 examines the unload door open switch, passing control to wait unit 467 until the unload door open switch is closed. Then unit 468 energizes the pull rod to pull the basket from a washer sterilizer, and control passes to the unit 469 which examines the status of the basket-removed switch, which is closed when the basket is pulled from the vessel. Until it is closed control is passed to a wait unit 470 and, after closure control passes to a unit 471 which examines the state of the pull-rod-return switch, passing control to a wait unit 472 until the pull-rod-return switch is closed, signifying that the pull rod has returned to its home position outside the vessel.

Unit 473 energizes the close-unload-door solenoid and unit 474 examines the state of the unload-door switch, passing control to the wait unit 475 until the unload-door switch is closed, signifying that the unload door is closed. Then unit 476 turns off the unload lamp, unit 477 de-energizes the hydraulic pump, and a unit 479 turns on the print lamp and causes the printer to print out the data which was previously stored, so that the times and conditions of the entire cycle of operation are all printed out together. Then unit 479a receives control and passes control to a wait unit 479d until printing is complete, after which unit 479b turns off the print lamp and the unit 479c turns on the ready lamp and causes the printer to print. The operation described above repeats as soon as the basket-ready switch is closed, signifying that a basket is ready on the feed conveyor to be loaded into the washer-sterilizer.

As indicated in FIG. 6, several of the control units described, in addition to operating one of the washer-sterilizer control, or controlling operation of the indicating lamps, cause time information to be stored. At the same time other data is stored, such as a designation of what cycle is entered at that time. For some cycles, such as the sterilize cycle, the temperature and pressure is also stored. Then at the end of the complete cycle of operation, all of the data is printed out. For example, "12:02.35 wash", indicating that the wash cycle was entered at 2.35 minutes after 12 o'clock. Thus, the cycles performed are logged out by the printer, in the form of a line of print indicating the time of occurrence of each operation. The printed record produced by the printer 47 provides a record of the washer-sterilizer process, so that correct operation of the equipment can be confirmed at a later time, if necessary. In addition, the information may be stored in the CPU 50 or in its peripheral storage devices. This is especially useful in connection with hospital procedures, so that the operation of the washer-sterilizer apparatus can be removed from suspicion in the resolution of any contamination inquiry, since the printed record produced by the printer proves proper operation of the washer-sterilizer.

In the chain of control units illustrated in FIG. 6, it is frequently necessary to wait for a given control signal to be produced, indicating that the operations which have been designated by previous control signals have in fact occurred. When the required signals for some reason do not occur, the unit which then has control cannot pass control to the next unit. The time of residence of control in each cycle is timed by the controller 49, and if the control remains hung up in a single cycle more than a predetermined time, the CPU recognizes a fault condition, sounds an alarm indication, and maintains control in the unit having control at the time of the fault. In addition the occurrence of a fault is printed out by the printer 47, along with its time of occurrence, to call attention to the fact that a fault has occurred.

A diagram indicating the manner in which the controller 49 times each cycle is illustrated in FIG. 7. A control unit 500 resets an interval timer each time a signal is supplied to the CPU 50 to store the time of day when a cycle is entered. A unit 502 continually examines the interval timer to determine if the time has expired, and if not, passes control to a wait unit 504. As long as the apparatus is functioning properly, the interval timer will never time out, because it is reset by the store signal at the end of each cycle, over one of the lines 505. As the wash cycle has the longest normal interval (5 minutes) the timer is set for a time slightly in excess of 5 minutes. Then if any cycle maintains control for longer than 5 minutes, the timer times out, and control passes to a unit 506, which examines the sensing devices and determines whether the machine is in its ready condition. If so, no fault is indicated, and the alarm is not sounded. If the machine is not in a ready condition, however, a fault is indicated and control passes to units 508 and 509 which cause an alarm to be sounded and a fault condition printed out on the printer. In addition, unit 510 disables all outputs from the sensing devices, and so no further cycling of the machine takes place. This facilitates repair of the machine, because the circumstances of the fault can be determined from the state of the control units, e.g. which unit has control at the time of the fault.

The operation of the mode control switches 116-120 determines the mode of operation of the apparatus of the present invention in several different modes. When none are operated, thereby selecting the automatic mode, the operation of the apparatus is as has been described above. Other functions are performed when one of the switches 116-120 is operated.

When the equipment-not-in-service switch 116 is operated, for one of the washer-sterilizer units, the transport conveyor is inhibited from sending baskets to the feed conveyors of the affected unit, when it is in its ready condition, and the outputs of its sensing devices are de-energized or disabled. In addition, the printer prints an indication that the mode control switch has been moved to its equipment-not-in-service position, to furnish a record of this operation. When the alarm switch 120 is operated, all outputs of the controller 49 are disabled, and the controller is held in its then current position. A printed record of the alarm condition having been entered is printed out on the printer.

The equipment-not-in-service switch 116 is operated whenever an operator decides that that particular machine is not to be used. The alarm switch 117 is operated when the operator wants to stop the machine without waiting for a sterilization program to be concluded. This switch is used only on an emergency basis, because once it has been closed, the machine cannot be returned to automatic operation until an equipment test cycle and a quality assurance cycle have been completed, as described hereinafter.

The quality assurance transfer switch 118 is operated only after successful completion of an equipment test cycle and a quality assurance cycle, when the results of such cycles show the machine to be operating effectively. The results may include laboratory analysis of the effectiveness of operation, at intervals, by using a test load sent through a complete cycle of operation as a part of a maintenance procedure. The quality assurance transfer switch is then operated to make the machine available for automatic operation. Maintenance is indicated after an automatic cycle has failed for some reason, but preventive maintenance may be performed at any time. After any maintenance or repair operation, a quality assurance program is performed to insure proper operation before any regular articles are processed by the machine. The quality assurance cycle is performed with a special basket, the contents of which can be tested after processing to prove proper sterilizing operation.

If the quality assurance cycle is not successfully completed, an operator alarm is triggered, and the fault is printed out by the printer.

Referring now to FIG. 8, a diagram of an equipment maintenance program is illustrated. This program is entered by the operation of the normal maintenance switch 119 by a maintenance man, and unit 600 inhibits operation of the feed conveyor so that no additional baskets are delivered to the machine, and unit 601 stores an indication that a maintenance program is being performed. All the controller 49 outputs are de-energized by the unit 602, and control is passed to a unit 603 which turns on the drain lamp, and unit 604 which stores the drain time. The unit 605 opens the drain valve, and then control is passed to unit 606, which inspects the drain-closed switch, passing control to wait unit 607 until the switch is found to be closed. The steam-to-chamber solenoid is energized by unit 608, and the water-to-ejector solenoid and the water-to-condenser solenoid are operated by units 609 and 610.

Control then passes to a unit 613 which sets the drain timer. The drain cycle lasts for 20 seconds, and so the drain timer is set for a period of 20 seconds. The unit 614 inspects the timer, passing control to a wait unit 615 until the time is up, after which unit 611 examines the condition of the float switch, passing control to a wait unit 612 until the switch is found to be closed, after which unit 616 turns off the drain lamp and unit 617 turns on the exhaust lamp while unit 618 stores the time the exhaust cycle is entered.

Then the unit 619 de-energizes the steam-to-chamber solenoid, and the unit 620 inspects the signal generated by the pressure sensing device 124, passing control to a wait unit 621 until the pressure reaches 1.5 psi.

When a pressure of 1½ p.s.i. is reached, the unit 622 turns off the exhaust lamp, and unit 623 turns on the vacuum break lamp while unit 624 stores the vacuum break time. Then the water-to-ejector solenoid is de-energized by unit 625, the drain valve motor is energized by unit 626, and unit 627 inspects the drain-closed switch, passing control to a wait unit 628 until the switch indicates that the drain is fully closed. Then unit 629 de-energizes the water-to-condenser solenoid, and the vacuum brake solenoid is energized by unit 630.

Control then passes to unit 631, which examines the vacuum pressure within the vessel, passing control to a wait unit 632 until the pressure reaches ½ inch of mercury.

Control then passes to unit 633, which de-energizes the vacuum break solenoid, is de-energized while the unit 635 stores the unload time. Then the hydraulic pump motor circuit is energized by unit 637, to provide hydraulic pressure for unlocking the doors, and the door unlock solenoid is energized by the unit 638. The unit 639 examines the state of the door unlock switch until it is closed, signifying that the doors are unlocked, and passes control to a wait unit 640 until this event occurs. Then unit 641 de-energizes the hydraulic pump circuit, and unit 642 energizes a manually operable door control circuit, so a maintenance man can open and close the doors.

The execution of this program insures that the vessel is fully drained and the vacuum is broken before the doors are manually opened. This program is entered, under control of a maintenance man, after a fault, no matter where in the sterilizing program the fault is located.

Each step in the maintenance program is logged out by the printer, so that a record is maintained as to when maintenance is performed, together with proof of the proper execution of the program.

A preventive maintenance program is carried out when the preventive maintenance switch 119 is closed. In this program, the feed conveyor is inhibited, and the manual door circuit is immediately energized, provided the machine is in a ready condition, to permit manual opening and closing of the doors. This program is performed only when the machine is in a ready condition, so that there is no need to drain the vessel before allowing the doors to be operated.

From the foregoing it will be appreciated that the present invention provides a controller usable in connection with a hospital washing-sterilizing system, which provides a printed record of the time and circumstances under which each step of the programs are carried out. With the printed record, it is possible to verify proper operation of the washer-sterilizer units.

In a preferred embodiment of the present invention, an Industrial 14/35 controller is used as the controller 49; a PDP 8 is used as the CPU 50; and one of the many commercially available printers is used for the printer 47. Preferably, a VT14 Programming terminal, is used with the Industrial 14/35, as known to those skilled in the art. All of these devices are marketed by Digital Equipment Corporation. The washer-sterilizer units themselves are commercially available units, but are modified as described above to provide signals from sensing devices to the controller and to accept operating signals from the controller instead of from cam-operated switches and cam-operated valves. Program listings for the controller 49 and for the CPU 50 are submitted with this application.

Alternatively, a multistage shift register may be employed for the control units of FIGS. 6-8 with a source of clock pulses for shifting a single bit from state to stage throughout the shift register, each of the stages having an output connected to operate one of the controls, set a timer, operate the printer, etc. The clock pulses are connected to the shift register through gates which are enabled when the conditions are met for execution of the next step. For example, when a given switch must be closed before the next step can be performed, no gate is able to pass a clock signal until the switch has been closed, and the switch closure furnishes a signal to one of the inputs of a gate which has its other input enabled by the current output of the shift register. This construction performs the operations of the several wait units, without requiring separate physical devices for each wait unit. As the construction of a conventional shift register is well known in the art, it need not be described in detail.

The present invention, which has been described in terms of the control of washer-sterilizer units, is equally adaptable for control of other devices, such as a pulsating high vacuum, a gas sterilizer system, or the like. Such systems are controlled, step by step, using a controller constructed in the same manner as described above.

In addition, the provision of a neutral area in which all of the controls and apparatus to which a maintenance man must have access for routine and corrective maintenance, makes it unnecessary for a repairman to enter either the contaminated or the clean area, with the attendant reduction in the risk of contaminating material in the clean area, or being contaminated by organisms in the contaminated area.

Referring now to FIG. 9, a flow chart illustrates the equipment test cycle and the quality assurance cycle. A quality assurance cycle is undertaken each day, at 7 a.m. After every equipment maintenance procedure, an equipment test cycle is first conducted, after which a quality assurance cycle is performed. The machine cannot be returned to automatic operation unless the quality assurance transfer switch is closed. Since this switch is key operated, with the key in the possession of someone of authority, the machine cannot be returned to automatic condition unless authorized.

The program illustrated in FIG. 9 is entered each day at 7 a.m. over a line 650. The program is preferably entered by means of an interrupt which is responsive to the time of day clock. The line 650 is connected to a unit 652 which tests whether the machine is in its ready condition. If not, it may be completing an automatic cycle of operation, and control is passed to a wait unit 654 until the operation is completed and the machine is placed in its ready condition. The wait unit 654 is preferably an executive routine or the like so that the apparatus can complete other tasks while it is waiting for the machine to assume its ready state. When the ready condition is recognized by the unit 652, control passes to a unit 656 which inhibits automatic operation of the washer sterilizer, and passes control to a unit 658. The unit 658 examines the state of the equipment-not-in-service switch. If it is closed, control passes to a wait unit (not shown) and returns to the unit 658 until the equipment-not-in-service switch is opened. The wait unit, which is omitted from the drawing in the interest of simplicity, is preferably like the unit 654. Additional wait units omitted from FIG. 9 are also like the unit 654. When the equipment is taken out of service, it is not required to go through a quality assurance cycle until such time as it is to be returned to service. When the equipment-not-in-service switch is open, control passes to the unit 664 which examines the state of the preventative maintenance and normal maintenance switches. If either of them are closed, control passes to a wait unit (not shown), and returns to the unit 664. This insures that the quality assurance cycle will not be initiated until after the maintenance procedures are performed. When the preventative maintenance and normal maintenance switches are open, control passes to a unit 666, and the printer prints a notice that the machine is ready for a quality assurance cycle. The operator then places a specially loaded quality assurance basket in place at the entrance of the machine. The unit 668 examines the state of the basket-ready switch and passes control to a wait unit (not shown) until the switch is found to be closed. Control then passes, via a unit 670, to the first step of the automatic program, and the entire cycle is run, through all of the stages described above in connection with FIGS. 6A-6H. At the end of the entire cycle, control is passed to a unit 674 which determines whether the quality assurance cycle was completed satisfactorily. The cycle is successful if it would have been returned to its ready condition at the conclusion of the cycle if it has been run in its automatic mode. Of course, the unit 656 prevents this from actually occurring. If the cycle is completed satisfactorily, control is passed to unit 676, which examines the state of the quality assurance transfer switch. If it is not closed, control is passed to a wait unit 678 and then returned to the unit 676 until the switch is closed. As noted above, the quality assurance transfer switch is a key operated switch, and can be closed only by a person of authority, so that inadvertent closure of the switch under conditions which are not optimum can be avoided. The unit 676 then passes control to the unit 680 which turns on the ready light; then the unit 682 causes the printer to print that a notice that the equipment is ready for service, and the unit 684 enables automatic operation of the apparatus, so that when a basket is in position, a complete sterilizing operation will be initiated and performed automatically.

If the quality assurance cycle is not satisfactorily completed, the unit 674 selects a branch 686 which passes control to a unit 688, which inspects the state of the automatic alarm or the operator alarm switch. Normally a failure of the quality assurance cycle will be accompanied by the automatic alarm switch being closed. If not, control is passed to a wait unit (not shown) until the operator alarm switch is closed, after which control is passed over a line 692 to a unit 694. The unit 694 examines the state of the normal maintenance switch. If it is not closed, control passes to a wait unit (not shown) and returns to the unit 694 until the switch is closed. This operation insures that after the failure of a quality assurance cycle, some maintenance procedures will be effected before the operation can resume. When the normal maintenance switch is closed, control is passed from the unit 694 to the unit 600 (FIG. 8A) which has already been described above in connection with maintenance procedures. The sequence of events described in FIGS. 8A and 8B cause the machine to be operated in such a way to insure that the machine is drained and the pressure is brought to atmospheric level before the door is opened. This is necessary because the failure of a quality assurance cycle may leave the machine in nearly any condition, and the procedures illustrated in FIGS. 8A and 8B are necessary before the doors can be safely open to allow access to the interior of the machine.

Control is then passed to unit 700 which examines the state of the equipment-not-in-service switch. If it is closed control passes to a wait unit (not shown) and returns to the unit 700. When the equipment-not-in-service switch is open, control passes to unit 704 which examines the state of the preventative maintenance and the normal maintenance switches. If either one is closed, control passes to a wait unit (not shown) and returns to unit 704. Otherwise, control passes to a unit 708 which causes the printer to print a notice that the equipment is ready for a test cycle. The maintenance man then places a basket at the entrance position, closing the basket-ready switch.

Unit 709 is given control when the equipment-not-in-service switch is closed, and passes control to the unit 656.

Control passes to unit 710 which inspects the condition of the basket-ready switch, passing control to a wait unit (not shown) until the basket-ready switch is found to be closed. Then control passes to a unit 714 which causes the entire cycle to be run, as described above in connection with FIGS. 6A-6H. At the conclusion of the entire cycle, control passes to unit 716 which determines whether it has been completed successfully. If not, control branches over line 718 to the unit 688, the function of which has been described above. When the test cycle is completed satisfactorily, control passes to the unit 666 which causes the printer to print out an indication that the equipment is ready for a quality assurance cycle. Subsequent events are the same as described above.

In the operation described above, the unit 694 receives control from the unit 688, following an unsuccessful completion of a quality assurance cycle or a test cycle. The unit 694 can also receive control, however, by the closing of the normal maintenance switch, any time normal maintenance is indicated.

When the preventative maintenance switch is closed, the sequence is entered via unit 718. Then control passes over a line 720 to a unit 722 which examines the state of the machine to see if it is in the ready condition. If not, control passes to wait unit (not shown), and control is returned to the unit 722. When the machine is found to be in its ready condition, control passes to a unit 724 which inhibits further automatic operation, after which control passes to a unit 700. Subsequent events are the same as described above.

The difference in the operation steps following closing of the normal maintenance and preventative maintenance switches flows from the fact that the normal maintenance switch may be closed when the equipment is in any condition, after having failed to complete a cycle, while the preventative maintenance switch is closed when the machine is operating normally, and interrups operation of the machine only after the completion of a normal automatic cycle.

It can be seen from the foregoing that any time the machine undergoes maintenance, whether normal maintenance or preventative maintenance, a test cycle and then a quality assurance cycle must be performed before the machine can be returned to its automatic mode. The test cycle must be successfully completed before the quality assurance cycle is performed, so that the quality assurance cycle is always performed after maintenance, subsequent to an indication that the machine is operating properly from a mechanical point of view. If the maintenance procedures have been ineffective or incomplete, a subsequent test cycle is required, with successful completion, before a quality assurance cycle can be executed. In any event, following a successful test cycle, a quality assurance cycle must be performed, and a quality assurance cycle must also be performed at 7 a.m. each day, unless the machine remains out of service that day. If the quality assurance cycle, whenever performed, is not successfully completed, the equipment goes into its maintenance mode, to allow maintenance procedures to be performed, after which an equipment test cycle and a further quality assurance cycle must be performed.

After successful completion of a quality assurance cycle, the machine can be returned to its automatic mode of operation only by an authorized person, through the use of a key switch. In this way automatic use of the machine can be delayed until the special contents of the quality assurance cycle basket are investigated, if desired, to insure proper sterilization of the contents.

It is apparent that other modifications and additions may be made in the system of the present invention without departing from the essential features of novelty thereof, which are intended to be defined and secured by the appended claims.

What is claimed is:

1. In a sterilizing system having sterilizing apparatus for sterilizing articles, said sterilizing apparatus having an inlet door opening into a contaminated area, an outlet door opening into a clean area, and means for opening and closing said doors one at a time; a neutral zone adjacent said sterilizing apparatus defined by a first wall aligned with said inlet door for separating a contaminated area from said neutral zone and a second wall aligned with said outlet door for separating a clean area from said neutral zone, and including means for supporting controls for said sterilizing apparatus within said neutral zone.

2. Apparatus according to claim 1, including a platform disposed in said neutral zone above said sterilizing apparatus, for supporting a maintenance man thereon, and means for mounting controls for said apparatus within said neutral zone above said platform.

3. Apparatus according to claim 2, including means for mounting said controls on one of said walls within said neutral zone.

4. Apparatus according to claim 2, including means for connecting said controls with said sterilizing apparatus.

5. Apparatus according to claim 1, including a controller disposed in a neutral area, means for isolating said neutral area from said contaminated area and from said clean area, and means for connecting said controller with said controls, whereby operating signals from said controller operate said controls.

6. Apparatus according to claim 5, wherein said sterilizing apparatus has a plurality of sensing devices associated therewith, and means for connecting said sensing devices with said controller, whereby said controller operates said controls in response to detection of predetermined signals from said sensing devices.

7. Apparatus according to claim 6, including a printer, and means for connecting said printer to said controller, whereby said printer prints a printed record of operating signals developed by said controller for operating said controls.

8. Apparatus according to claim 6, including timing means, and means for connecting said timing means with said controller for causing said printer to print the times of occurrence of said operating signals.

9. Apparatus according to claim 5, wherein said controller includes timing means, means for setting said timing means for a predetermined time interval, and means for halting operation of said controller in response to the non-occurrence of an operating signal within said interval.

10. In a washer-sterilizer system having at least one sterilizing machine with a sterilizing chamber, means for introducing articles through an entry door into said chamber in unsterilized condition from a supply area, means for withdrawing articles through an exit door from said chamber in sterilized condition into a sterilized area separate from said supply area, a plurality of controls for said machine for regulating the temperature and pressure within said chamber during a sterilizing process, and for preventing operation of said entry and exit doors during said process, a plurality of sensing devices for sensing the temperature and pressure within said chamber during said sterilizing process, timing means for producing signals indicative of the occurrence of predetermined time intervals, and an automatic controller connected to said control devices, to sensing devices and to said timing means for causing said sterilizing machine to carry out a predetermined sequence of steps, including inhibiting operation of said doors after said articles have been introduced into said chamber through said entry door, controlling a sequence of elevated temperatures and elevated pressures including at least one step in which a predetermined temperature is maintained within said chamber for a predetermined time interval, and discontinuing the prevention of operation of said exit door subsequent to said chamber returning to atmospheric pressure on completion of said program, wherein said automatic controller includes means for initiating each step of said sequence in response to a completion signal from said sensing devices indicating that the preceding step in said sequence has been completed, and inhibiting means responsive to non-receipt of a completion signal for inhibiting occurrence of further steps of said sequence.

11. Apparatus according to claim 10, including timer means for producing a signal indicating the time of day, and printer means connected to said timer means and to said automatic controller for automatically printing a record of the time of occurrence of each step of said sequence.

12. Apparatus according to claim 11, wherein said automatic controller includes means for causing said printer to print a record of the time at which said inhibiting means inhibits further steps of said sequence.

13. Apparatus according to claim 10, including disabling means responsive to said inhibiting means for disabling said automatic controller from automatically controlling further sequences subsequent to operation of said inhibiting means.

14. Apparatus according to claim 13, including means responsive to said disabling means for permitting manual operation of said sterilizing machine following operation of said inhibiting means.

15. Apparatus according to claim 14, including means responsive to manual operation of said sterilizing machine following operation of said inhibiting means for disabling said inhibiting means and allowing further automatic operation of said sterilizing machine by said automatic controller.

16. Apparatus according to claim 10 including printer means connected to said automatic controller and to said inhibiting means for automatically printing a record in response to the condition of said automatic controller at the time of operation of said inhibiting means.

17. Apparatus according to claim 16, wherein said automatic controller includes a plurality of control units for performing individual ones of said sequence of steps, said printer means being operative in response to operation of said inhibiting means for printing an identification of the control unit having control of said washer-sterilizer system at the time of operation of said inhibiting means.

18. A method of controlling operation of a hospital sterilizing machine for sterilizing articles, comprising the steps of providing a plurality of sensing devices for sensing temperature, pressure and operating conditions within the machine, providing a plurality of controls for altering conditions of temperature and pressure within the interior of the machine, providing an automatic controller for operating said controls in step-by-step fashion in response to predetermined signals from said sensing devices, detecting the absence of one of said signals, indicative of a fault condition, and halting operation of said controls in response to said detection.

19. The method according to claim 18, including the steps of providing a printer for said controller, and causing said printer to make a printed record of predetermined operations of said controller.

20. In apparatus for controlling the operation of a hospital sterilizing machine for sterilizing articles introduced into said machine from an unsterile area, said machine being adapted to discharge sterilized articles into a clean area separated from said unsterile area, control means normally operative for controlling said machine in an automatic mode, interrupting means connected to said control means for interrupting the automatic operation of said control means on the occurrence of predetermined conditions, and switch means connected to said control means for restoring said control means to its normal automatic operation, said switch means being operative in response to completion of a cycle of operation subsequent to said interruption.

21. Apparatus according to claim 20, wherein said switch means comprises key switch means, whereby said key switch means is normally locked and its operation is restricted to persons having access to a key for said key switch means.

22. Apparatus according to claim 20, including means for rendering said switch means ineffective until said sterilizing apparatus has been cycled through a quality assurance cycle.

23. Apparatus according to claim 20, including a maintenance switch, means for interrupting the operation of said control means in response to the operation of said maintenance switch, and means for rendering said switch means ineffective following operation of said maintenance switch until said sterilizing apparatus has been cycled through a quality assurance cycle.

24. Apparatus according to claim 23, including means for rendering said switch means ineffective following operation of said maintenance switch until said sterilizing apparatus has been cycled first through an equipment test cycle and then said quality assurance cycle.

* * * * *

UNITED STATES PATENT AND TRADEMARK OFFICE
CERTIFICATE OF CORRECTION

PATENT NO. : 4,067,691
DATED : January 10, 1978
INVENTOR(S) : Donald L. McGady, Thomas M. Hooper & Joseph E. Wilczynski It is certified that error appears in the above-identified patent and that said Letters Patent are hereby corrected as shown below:

Column 5, line 50, cancel "unloaded" and insert --unload--.

Column 7, line 49, before functional, cancel "a" and insert

--in--.

Column 7, line 66, cancel "examle" and insert --example--.

Column 9, line 45, after 332 cancel "unit" and insert --until--.

Column 9, line 49, cancel "pump" and insert --sump--.

Column 12, line 37, after "closure" insert --, --.

Column 17, line 30, cancel "has" and insert --had--.

Signed and Sealed this

Twenty-third Day of May 1978

[SEAL]

Attest:

RUTH C. MASON
Attesting Officer

LUTRELLE F. PARKER
Acting Commissioner of Patents and Trademarks